(12) United States Patent
Yamada et al.

(10) Patent No.: US 9,737,558 B2
(45) Date of Patent: Aug. 22, 2017

(54) PEYER'S PATCH ACTIVATOR

(71) Applicants: Mitsui Sugar Co., Ltd., Tokyo (JP); The Kitasato Institute, Tokyo (JP)

(72) Inventors: Haruki Yamada, Tokyo (JP); Hiroaki Kiyohara, Tokyo (JP); Kazuhiko Otoguro, Tokyo (JP); Aki Ishiyama, Tokyo (JP); Masato Iwatsuki, Tokyo (JP); Satoshi Omura, Tokyo (JP); Masami Mizu, Tokyo (JP); Toshikazu Kawai, Tokyo (JP); Jun Kashimura, Hyogo (JP); Kenji Koge, Tokyo (JP)

(73) Assignees: Mitsui Sugar Co., Ltd., Tokyo (JP); The Kitasato Institute, Tokyo (JP)

( * ) Notice: Subject to any disclaimer, the term of this patent is extended or adjusted under 35 U.S.C. 154(b) by 0 days.

(21) Appl. No.: 14/432,315

(22) PCT Filed: Sep. 18, 2013

(86) PCT No.: PCT/JP2013/075152
§ 371 (c)(1),
(2) Date: Mar. 30, 2015

(87) PCT Pub. No.: WO2014/054421
PCT Pub. Date: Apr. 10, 2014

(65) Prior Publication Data
US 2015/0258131 A1 Sep. 17, 2015

(30) Foreign Application Priority Data
Oct. 2, 2012 (JP) ................ P2012-220341

(51) Int. Cl.
| | | |
|---|---|---|
| *A61K 31/716* | (2006.01) | |
| *A61K 31/715* | (2006.01) | |
| *A61K 36/899* | (2006.01) | |
| *A61K 31/137* | (2006.01) | |
| *A61K 31/635* | (2006.01) | |
| *A61K 31/505* | (2006.01) | |
| *A61K 31/49* | (2006.01) | |
| *A61K 31/4709* | (2006.01) | |
| *A61K 31/357* | (2006.01) | |
| *C08B 37/00* | (2006.01) | |
| *C08L 5/00* | (2006.01) | |
| *A61K 31/4706* | (2006.01) | |
| *A23K 20/163* | (2016.01) | |
| *A23L 33/10* | (2016.01) | |
| *A23L 33/105* | (2016.01) | |

(52) U.S. Cl.
CPC ......... *A61K 31/716* (2013.01); *A23K 20/163* (2016.05); *A23L 33/10* (2016.08); *A23L 33/105* (2016.08); *A61K 31/137* (2013.01); *A61K 31/357* (2013.01); *A61K 31/4706* (2013.01); *A61K 31/4709* (2013.01); *A61K 31/49* (2013.01); *A61K 31/505* (2013.01); *A61K 31/635* (2013.01); *A61K 36/899* (2013.01); *C08B 37/0003* (2013.01); *C08B 37/006* (2013.01); *C08L 5/00* (2013.01); *A23V 2002/00* (2013.01)

(58) Field of Classification Search
CPC .. A61K 31/716; A61K 31/715; A61K 36/899; A23L 33/105
See application file for complete search history.

(56) References Cited

U.S. PATENT DOCUMENTS

| | | | | |
|---|---|---|---|---|
| 7,150,885 B2* | 12/2006 | Araki | ............ | A23L 1/3002 424/184.1 |
| 2003/0147978 A1* | 8/2003 | Araki | ............ | A23K 1/1646 424/750 |
| 2004/0038933 A1* | 2/2004 | Kaneko | ............ | A61K 31/715 514/54 |

FOREIGN PATENT DOCUMENTS

| | | |
|---|---|---|
| JP | S57-106624 A | 7/1982 |
| JP | 2000-297046 A | 10/2000 |
| JP | 2003-063975 A | 3/2003 |
| JP | 2008-208102 A | 9/2008 |
| JP | 2010-285421 A | 12/2010 |
| WO | 03/099309 A1 | 12/2003 |
| WO | 2008/152207 A1 | 12/2008 |
| WO | 2012/007577 A1 | 1/2012 |
| WO | 2012/115994 A1 | 8/2012 |

OTHER PUBLICATIONS definition of prevent, Oxford English Dictionary Online, http://dictionary.oed.com/, accessed online Mar. 27, 2010, especially definition 9a. at p. 2.*
"Malaria—Travelers—Choosing a Drug to Prevent Malaria", CDC web page, https://www.cdc.gov/malaria/travelers/drugs.html, accessed online on Aug. 1, 2016.*
McElroy et al., Am. J. Trop. Med. Hyg., 51(5), 1994, p. 523-532.*
Ntonifor et al., "Traditional use of Indigenous Mosquito-Repellents to Protect Humans Against Mosquitoes and Other Inspect Bites in a Rural Community of Cameroon," East African Medical Journal, 83: 553-558 (2006).
Extended European Search Report issued in counterpart European Patent Application No. 13844047.4 dated May 10, 2016.
El-Abasy et al., "Immunostimulating and Growth-Promoting Effects of Sugar Cane Extract (SCE) in Chickens," Journal of Veterinary Medical Science, 64: 1061-1063 (2002).
El-Abasy et al., "Protective Effects of Sugar Cane Extracts (SCE) on Eimeria tenella Infection in Chickens," Journal of Veterinary Medical Science, 65: 865-871 (2003).

(Continued)

*Primary Examiner* — Jonathan S Lau
(74) *Attorney, Agent, or Firm* — Morgan, Lewis & Bockius LLP

(57) ABSTRACT

The present invention provides a Peyer's patch activator containing a polysaccharide obtained from sugar cane as an active ingredient, wherein the polysaccharide contains α-glucan as a main component and has a peak molecular weight within a range of 720,000 to 1,080,000, with a proportion of glucose in all component sugars being 80% or more, and proportions of nonreducing terminal glucose and α-1,6-linked glucose being 20 to 30% and 15 to 25%, respectively.

18 Claims, 10 Drawing Sheets

(56) References Cited

OTHER PUBLICATIONS

Askling et al., "Management of imported malaria in Europe," Malaria Journal, 11: Article 328 (2012).
Kaminogawa et al., "Research on the evaluation of the effects of so-called health food-establishment of evaluation methods for the immunoregulatory and allergy prevention functions of food," Research on the evaluation of the effects of so-called health food, Heisei 17 Nendo Sokatsu Buntan Kenkyu Hokokusho, 11-20 (2006) (see partial English translation).
Li et al., "Activation of the classical complement pathway by a polysaccharide from sugar cane," Immunopharmacology, Medline [online] United States National Library of Medicine, Retrieved from: STN, Medline Accession No. 1983030185, 5: 31-38 (1982).
Nakasone et al., "Water soluble polysaccharides in cane juice obtained by the diffusion system," Science Bulletin of the College of Agriculture, University of the Ryukyus, 175-181 (1980).
Hong et al., "Enhanced production of hematopoietic growth factors through T cell activation in Peyer's patches by oral administration of Kampo (Japanese herbal) medicine, Juzen-Taiho-To," Phytomedicine, 5: 353-360 (1998).
Zasshi, Elucidation of Responsible Carbohydrate Chains in Activated beta-D-(1->3,6)-Galactan-Containing Polysaccharide and Pectin-like Polysaccharide from Atractylodes lancea and aboveground parts of Astragalus mongholicus, The Pharmaceutical Society of Japan, 128: 709-716 (2008) (see partial English translation).
International Preliminary Report on Patentability and Written Opinion issued in corresponding International Patent Application No. PCT/JP2013/075152 dated Apr. 16, 2015.
International Search Report issued in corresponding International Patent Application No. PCT/JP2013/075152 dated Nov. 19, 2013.

* cited by examiner

*Fig.10*
(A)
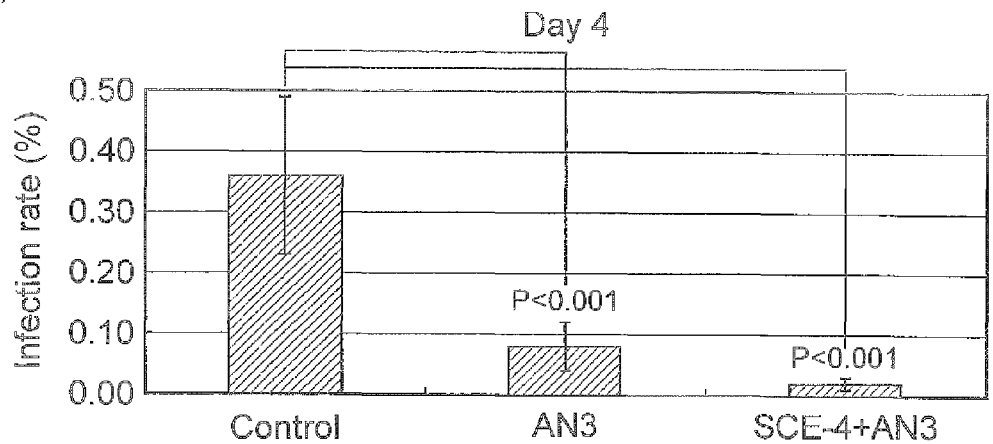
(B)
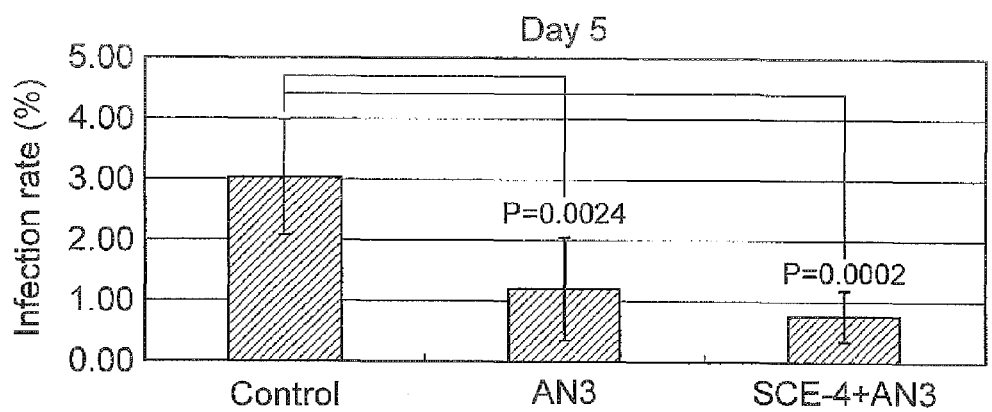
(C)
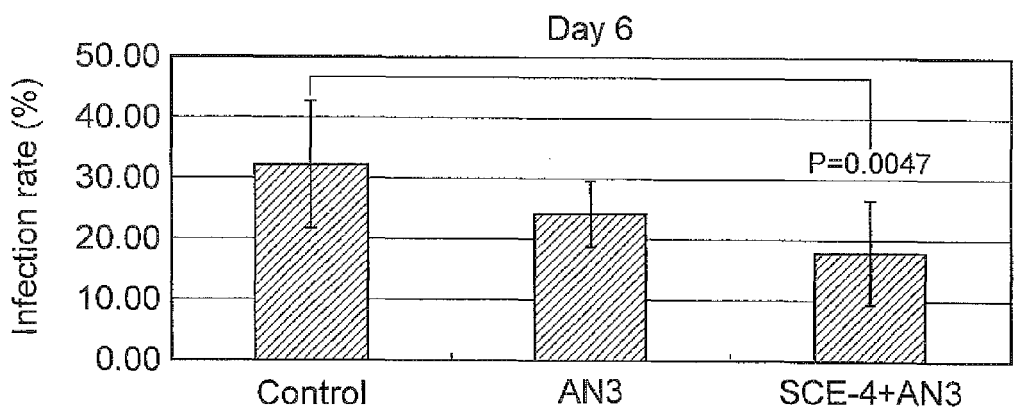

PEYER'S PATCH ACTIVATOR

TECHNICAL FIELD

The present invention relates to a Peyer's patch activator.

BACKGROUND ART

Peyer's patches are highly functionalized lymphoid follicle tissues present in the upper intestinal tract, and are one of inductive tissues serving as an important starting point for the production of antigen-specific secretory IgA and the expression of immunological tolerance. It is known that Peyer's patches play an important role in an immune system that is related to biophylaxis and called intestinal immunity. For example, because of the homing phenomenon, the lymphocytes of Peyer's patches are constantly recruited to the tissues of other local mucosal immune systems and systemic immune systems and function to transmit the immunological information.

As an example of Peyer's patch immune function modulating activity, the production of bone marrow cell growth promoting factors (e.g., cytokines) in Peyer's patches can be mentioned. As such a bone marrow cell growth promoting factor, for example, IL-6, which is a cytokine produced by immunocompetent cells in Peyer's patches, is known (Non-Patent Literature 1).

Meanwhile, it has already been reported that polysaccharides obtained from a rhizome of Atractylodes lancea DC and polysaccharides obtained from an aerial part of Astragalus mongholics Bunge have Peyer's patch immune function modulating activity (Non-Patent Literature 2).

In addition, there are known a preventive/therapeutic agent for infection, a vaccine adjuvant agent, and a preventive/therapeutic agent for diseases in humans or animals caused by Coccidia, which contain as an active ingredient an extract derived from sugar cane that is a gramineous plant (Patent Literatures 1 and 2).

CITATION LIST

Patent Literature

Patent Literature 1: JP-A-2000-297046
Patent Literature 2: JP-A-2003-63975

Non Patent Literature

Non-Patent Literature 1: T. Hong, T. Matsumoto, H. Kiyohara and H. Yamada: Enhanced production of hematopoietic growth factors through T cell activation in Peyer's patches by oral administration of Kampo (Japanese herbal) medicines, 'Juzen-taiho-to', Phytomedicine, Vol. 5, pp. 353 to 360 (1998)

Non-Patent Literature 2: Hiroaki Kiyohara, Toshiake Matsuzaki, Tsukasa Matsumoto, Takayuki Nagai, Haruki Yamada: Yakugaku Zasshi, Vol. 128, No. 5, pp. 709 to 719 (2008)

SUMMARY OF INVENTION

Problems to be Solved by the Invention

Artificially making possible Peyer's patch immune function modulation makes possible modulation of the immune system related to biophylaxis, and thus is beneficial. As disclosed in Non-Patent Literature 2, some substances having Peyer's patch immune function modulating activity are already known. However, it still cannot be said that the repertory is enough to meet the various needs of consumers.

In addition, although some functional components derived from a gramineous plant are already known, a component having Peyer's patch immune function modulating activity, for example, a component that has an enhancing effect on the production of cytokines having bone marrow cell growth promoting activity in Peyer's patches (hereinafter, this effect is also referred to as a "Peyer's patch activating effect"), has not heretofore known.

In view of the above circumstances, an object of the present invention is to provide a novel Peyer's patch activator that has an enhancing effect on the production of cytokines having bone marrow cell growth promoting activity in Peyer's patches.

Means for Solving the Problems

The present inventors have found that an $\alpha$-glucan fraction and a heteroglycan fraction purified from a sucrose-removed extract of Saccharum officinarum (sugar cane), which will be described below, have an enhancing effect on the production of cytokines having bone marrow cell growth promoting activity in Peyer's patches, and thus have accomplished the present invention.

That is, the present invention provides a Peyer's patch activator containing a polysaccharide obtained from sugar cane as an active ingredient.

The Peyer's patch activator of the present invention at least has an enhancing effect on the production of cytokines having bone marrow cell growth promoting activity (e.g., IL-6) in Peyer's patches. Therefore, at least by modulating the cytokine production in Peyer's patches, the Peyer's patch immune function modulating activity can be exerted. In addition, sugar cane is one of those that have been used as food products since ancient times, and therefore, a Peyer's patch activator with higher safety can be provided.

The polysaccharide may contain $\alpha$-glucan as a main component and have a peak molecular weight within a range of 720,000 to 1,080,000, with a proportion of glucose in all component sugars being 80% or more, and proportions of nonreducing terminal glucose and $\alpha$-1,6-linked glucose being 20 to 30% and 15 to 25%, respectively (hereinafter also referred to as an "$\alpha$-glucan fraction"). As a result, a more excellent Peyer's patch activating effect can be attained. Incidentally, "$\alpha$-1,6-linked glucose" herein means an $\alpha$-glucose unit linked with other structural units at hydroxyl groups of the position 1 and position 6, and is also referred to as "$\alpha$-6-linked glucose."

A "molecular weight distribution curve" herein means a distribution curve obtained from analysis of a molecular weight of each test sample (an $\alpha$-glucan fraction and a heteroglycan fraction) by high-speed gel filtration chromatography (HPSEC). The molecular weight is calculated, for example, from retention time of a test sample based on a calibration curve of molecular weight/retention time coefficient (Kav) created from retention time of a standard polysaccharide (pullulan P-800, 400, 200, 100, 50, 20, 10 and 5, Showa Denko) in HPSEC. In addition, HPSEC conditions can be set as follows, for example.

Column; coupled column, Asahi-pak GS710 and Asahi-pak GS620 (each 0.76 i.d.×60 cm) (Showa Denko)
Pump system; JASCO PV-980 (Jasco)
Detector; Shodex RI SE-62 (Showa Denko) (sensitivity: ×2)
Eluent; 0.2 M NaCl (1.0 mL/min)

A "peak molecular weight" herein means a molecular weight corresponding to a peak top of a peak in the "molecular weight distribution curve" mentioned above.

In addition, preferably, the α-glucan fraction is obtained from a fraction obtained by ethanol-precipitating a raw material selected from a sugar cane extract and a molasses derived from sugar cane, and removing low-molecular-weight substances from the obtained precipitate by dialysis or a membrane process (also referred to as an "ethanol-precipitated fraction").

The ethanol-precipitated fraction may also be obtained using a sugar cane extract or a molasses derived from sugar cane as it is. In addition, preferably, the ethanol-precipitated fraction is obtained using a fraction which absorbs light at a wavelength of 420 nm and from which sucrose, glucose, and fructose are excluded, among a large number of fractions obtained by passing a sugar cane extract or a molasses derived from sugar cane through a column filled with a cation exchange resin as a carrier and performing fractionation by a difference in affinity between the cation exchange resin and each component using water as an eluent (also referred to as an "extract derived from sugar cane"). By using the extract derived from sugar cane, the ethanol-precipitated fraction can be obtained more efficiently.

Preferably, the α-glucan fraction is a fraction obtained by passing the ethanol-precipitated fraction through a column filled with an anion exchange resin as a carrier, eluting components adsorbed on the anion exchange resin with an elution solvent having a low ionic strength to obtain eluted fractions, and further gel-filtering the obtained eluted fractions.

Preferably, the α-glucan fraction is a fraction in an amount corresponding to void volume of first outflow resulting from passing the ethanol-precipitated fraction through a column filled with an anion exchange resin equilibrated with water as a carrier, eluting components adsorbed on the anion exchange resin with 100 mM $NH_4HCO_3$ to obtain eluted fractions, and further passing the obtained eluted fractions through a gel filtration column having a molecular cutoff of $2 \times 10^3$ to $4 \times 10^5$ Da.

The polysaccharide may contain heteroglycan as a main component and have peak molecular weights within a range of 38,400 to 57,600 and within a range of 664,000 to 996,000, with proportions of glucose and arabinose in all component sugars being 30% to 50% and 20 to 30%, respectively, and a proportion of nonreducing terminal arabinose being 20 to 30% (hereinafter also referred to as a "heteroglycan fraction"). As a result, a more excellent Peyer's patch activating effect can be attained.

Preferably, the heteroglycan fraction is obtained from the ethanol-precipitated fraction. In this case, preferably, the ethanol-precipitated fraction is obtained from the extract derived from sugar cane.

Preferably, the heteroglycan fraction is a fraction obtained by passing the ethanol-precipitated fraction through a column filled with an anion exchange resin as a carrier, and eluting components adsorbed on the anion exchange resin with an elution solvent having a high ionic strength.

Preferably, the heteroglycan fraction consists of:

a fraction other than a fraction in an amount corresponding to void volume of first outflow resulting from passing the ethanol-precipitated fraction through a column filled with an anion exchange resin equilibrated with water as a carrier, eluting components adsorbed on the anion exchange resin with 100 mM $NH_4HCO_3$ and subsequently with 300 mM $NH_4HCO_3$ to obtain eluted fractions, and further passing the obtained eluted fractions through a gel filtration column having a molecular cutoff of $1 \times 10^4$ to $1 \times 10^6$ Da; and a fraction in an amount corresponding to void volume of first outflow resulting from passing the ethanol-precipitated fraction through a column filled with an anion exchange resin equilibrated with water as a carrier, eluting components adsorbed on the anion exchange resin with 300 mM $NH_4HCO_3$ and subsequently with 1.8 M $NH_4HCO_3$ to obtain eluted fractions, and further passing the obtained eluted fractions through a gel filtration column having a molecular cutoff of $2 \times 10^3$ to $4 \times 10^5$ Da.

The polysaccharide may be obtained by ethanol-precipitating a raw material selected from a sugar cane extract and a molasses derived from sugar cane, and removing low-molecular-weight substances from the obtained precipitate by dialysis or a membrane process (equivalent to the "ethanol-precipitated fraction").

The Peyer's patch activator of the present invention has a Peyer's patch activating effect and thus can also be used as an intestinal immune enhancer. In addition, through its intestinal immunity enhancing effect, the Peyer's patch activator can also be used, for example, as a preventive/therapeutic agent for *plasmodium* infection.

The Peyer's patch activator of the present invention can also be contained in food products, food additives, animal foods, pharmaceuticals, pharmaceutical additives, etc., and used.

The present invention also provides a medicine for preventing or treating *plasmodium* infection containing the Peyer's patch activator of the present invention.

The medicine for preventing or treating *plasmodium* infection may be used in combination with at least one antimalarial agent selected from the group consisting of quinine, mefloquine, sulfadoxine, pyrimethamine, chloroquine, primaquine, artesunate, artemether, and lumefantrine. Preferably, the antimalarial agent is artesunate.

The present invention can also be understood as use (or application) of the above-mentioned polysaccharide for activating Peyer's patches. In addition, the present invention can also be understood as a method for activating Peyer's patches, including a step of administering the above-mentioned polysaccharide to a subject.

Effects of the Invention

According to the present invention, a novel Peyer's patch activator is provided. According to the present invention, an agent containing a polysaccharide obtained from sugar cane as an active ingredient is administered to an animal (e.g., oral administration), whereby, for example, an enhancing effect on the production of cytokines (e.g., IL-6 as a bone marrow cell growth promoting factor) in Peyer's patches can be attained. As a result, for example, through the enhancement of intestinal immunity, the immune system related to biophylaxis can be enhanced.

In addition, the Peyer's patch activator of the present invention is derived from sugar cane that has been eaten by humans since ancient times, and therefore, the activator does not damage the health of humans or industrial animals such as domestic animals and domestic fowls for human consumption, and is safe.

BRIEF DESCRIPTION OF DRAWINGS

FIGS. 10(A) to 10(C) are graphs showing results of an oral administration test of a polysaccharide fraction in combination with an antimalarial agent in a rodent malaria parasite (chloroquine-resistant strain) infection model in Example 5.

EMBODIMENTS FOR CARRYING OUT THE INVENTION

Figure 1:
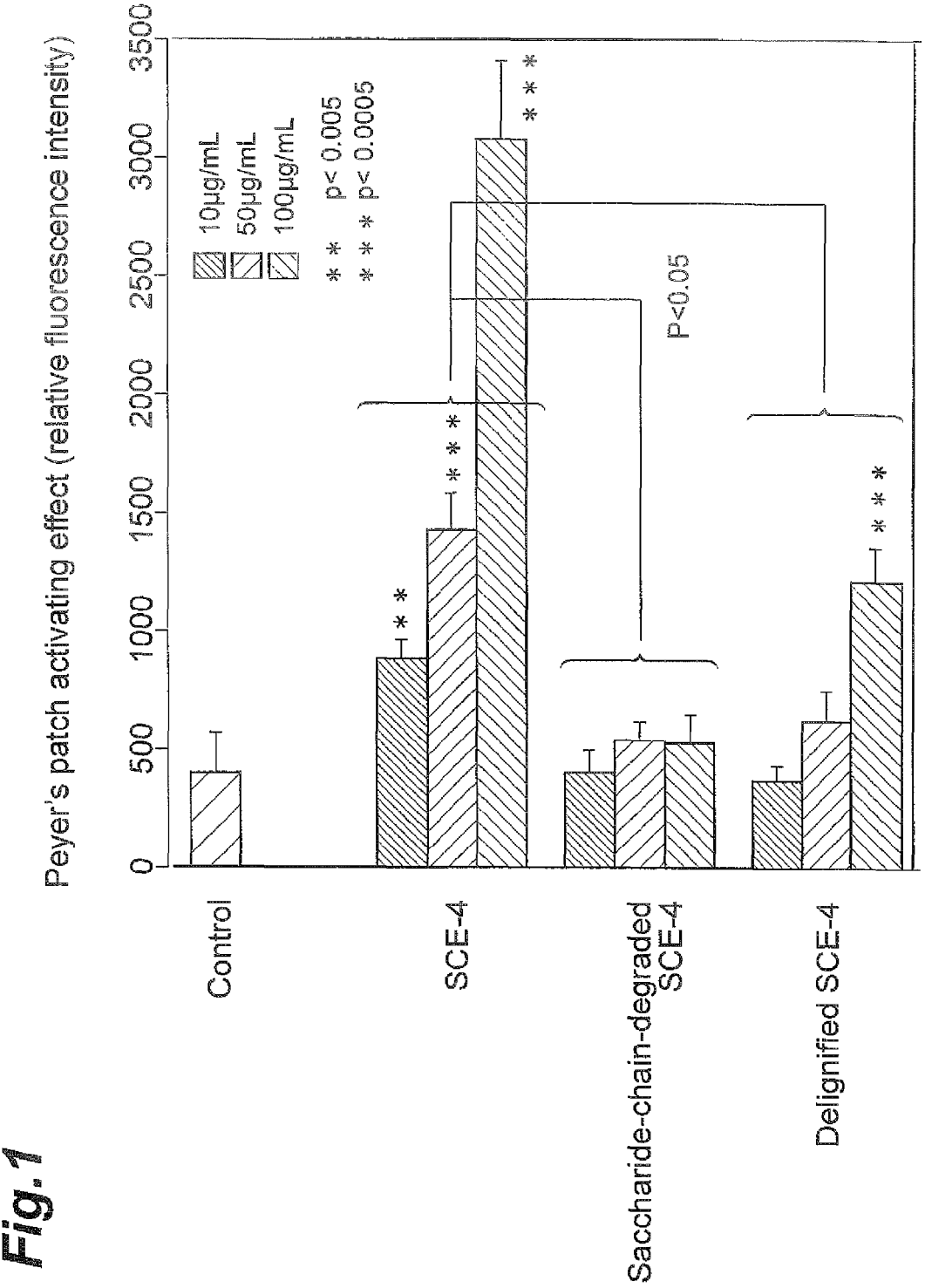
FIG. 1 is a graph showing results of a Peyer's patch activating effect test in Test Example 1.

Hereinafter, embodiments of the prevent invention will be described in further detail.

The Peyer's patch activator of the present invention contains a polysaccharide obtained from sugar cane as an active ingredient.

[Polysaccharide]

The polysaccharide obtained from sugar cane can be:

(i) one containing α-glucan as a main component and having a peak molecular weight within a range of 720,000 to 1,080,000, with a proportion of glucose in all component sugars being 80% or more, and proportions of nonreducing terminal glucose and α-1,6-linked glucose being 20 to 30% and 15 to 25%, respectively (α-glucan fraction);

(ii) one containing heteroglycan as a main component and having peak molecular weights within a range of 38,400 to 57,600 and within a range of 664,000 to 996,000, with proportions of glucose and arabinose in all component sugars being 30% to 50% and 20 to 30%, respectively, and a proportion of nonreducing terminal arabinose being 20 to 30% (heteroglycan fraction); or (iii) one obtained by ethanol-precipitating a raw material selected from a sugar cane extract and a molasses derived from sugar cane, and removing low-molecular-weight substances from the obtained precipitate by dialysis or a membrane process (ethanol-precipitated fraction).

Preferably, the α-glucan fraction further has a sugar content of 80 mass % to 90 mass % in terms of Glc. In addition, preferably, the α-glucan fraction has a uronic acid content of 5 mass % or less in terms of GalA. Preferably, the α-glucan fraction has a protein content of 10 mass % or less in terms of a bovine immunoglobulin. Further, preferably, the proportion of glucose in all component sugars of the α-glucan fraction is 75% to 90%.

The peak molecular weight of the α-glucan fraction only needs to be within a range of 720,000 to 1,080,000, but is preferably within a range of 810,000 to 990,000, more preferably within a range of 855,000 to 945,000. Preferably, the distribution range of the molecular weight of the α-glucan fraction in the molecular weight distribution curve is 16,000 to (a molecular weight corresponding to Vo volume), more preferably 16,000 to 1,660,000.

Preferably, the heteroglycan fraction further has a sugar content of 45 mass % to 55 mass % in terms of Glc. In addition, preferably, the heteroglycan fraction has a uronic acid content of 5 mass % to 10 mass % in terms of GalA. Preferably, the heteroglycan fraction has a protein content of 7.5 mass % or less in terms of a bovine immunoglobulin. Further, the proportions of glucose and arabinose in all component sugars of the heteroglycan fraction are preferably 30% to 40% and 22.5% to 27.5%, respectively.

The heteroglycan fraction has two peak molecular weights, one within a range of 38,400 to 57,600 and the other within a range of 664,000 to 996,000. The smaller peak molecular weight is preferably within a range of 43,200 to 52,800, and more preferably within a range of 45,600 to 50,400. The larger peak molecular weight is preferably within a range of 747,000 to 913,000, and more preferably within a range of 788,500 to 871,500. The heteroglycan fraction has at least two peaks in the molecular weight distribution curve. Preferably, the distribution range of the molecular weight of the heteroglycan fraction in the molecular weight distribution curve is 10,000 to (a molecular weight corresponding to Vo volume), more preferably 10,000 to 1,660,000.

[Polysaccharide Production Method]

<Ethanol-Precipitated Fraction>

The ethanol-precipitated fraction can be obtained by ethanol-precipitating a raw material selected from a sugar cane extract and a molasses derived from sugar cane, and removing low-molecular-weight substances from the obtained precipitate by dialysis or a membrane process. As the raw material used for ethanol precipitation, a sugar cane extract or a molasses derived from sugar cane may be used as it is, and it is preferable to use an extract derived from sugar cane in order to efficiently obtain the ethanol-precipitated fraction. The extract derived from sugar cane is a fraction which absorbs light at a wavelength of 420 nm and from which low-molecular-weight saccharides such as sucrose, glucose, and fructose are excluded, among a large number of fractions obtained by passing a raw material selected from a sugar cane extract and a molasses derived from sugar cane through a column filled with a cation exchange resin as a carrier and performing separation by a difference in affinity between the cation exchange resin and each component contained in the raw material using water as an eluent (by a difference in an elution rate). For the dialysis, a permeable membrane generally used for desalination can be used. In addition, for the membrane process, a UF membrane used for desalination, the removal of monosaccharides, etc., can be used.

A yield of the ethanol-precipitated fraction is, for example in the case of using an extract, usually about 5 mass % based on a solids content in the extract. In addition to polysaccharides, the ethanol-precipitated fraction also contains polyphenol, salts, and other components.

<Extract>

Hereinafter, a method for producing an extract derived from sugar cane will be described.

A sugar cane juice, a solvent extract of sugar cane or the like extract, or a molasses derived from sugar cane (hereinafter sometimes simply referred to as a "raw material") is passed through a column filled with a fixed carrier. The raw material can be used as it is, or can be adjusted to any concentration with water and used. Incidentally, in order to remove insoluble materials, it is desirable to filter the raw material prior to the treatment through a column. The filtration technique is not particularly limited, and techniques widely used in the food industry, such as screen filtration, diatom earth filtration, microfiltration, and ultrafiltration, can be used preferably.

A preferred aspect of the method that uses an ion exchange resin as a fixed carrier is as follows.

Ion exchange resins can be classified into cation exchange resins and anion exchange resins from the viewpoint of the nature of ion exchange. In the present invention, preferably, a cation exchange resin can be used. Further preferably, a strongly acidic type, sodium-ion type, or potassium-ion type cation exchange resin can be used. In addition, ion exchange resins are classified into gel-type resins, and porous resins such as a porous type, a microporous type, and a highly porous type, from the viewpoint of a resin form; however, in the present invention, preferably, a gel-type ion exchange resin can be used. Further preferably, a strongly acidic type, sodium-ion type, or potassium-ion type cation exchange resin in a gel type can be used. Such ion exchange resins are commercially available, and examples thereof include, as Diaion (trademark) series, SK1B, SK104, SK110, SK112, and SK116 (all trade names, Mitsubishi Chemical Corporation), and UBK530 and UBK550 (for chromatography separation, all trade names, Mitsubishi Chemical Corporation); as Amberlite (trademark) series, Amberlite IR120B, IR120BN, IR124, XT1006, and IR118, Amberlyst 31, and Amberlite CG120 and CG6000 for chromatography (all trade names, Organo Corporation); as Dowex (trademark) series, HCR-S, HCR-W2, HGR-W2, Monosphere 650C, Marason C600, 50Wx2, 50Wx4, and 50Wx8 (all trade names, Dow Chemical Company Japan), and Muromac 50WX (trade name, Muromachi Chemical Engineering Co., Ltd.); and as Purolite (trademark) series, C-100E, C-100, C-100x10, C-120E, PCR433, PCR563K, PCR822, PCR833, PCR866, PCR883, PCR892, and PCR945 (all trade names, AMP Ionex Corporation). Among them, the UBK series is particularly preferable.

An amount of the fixed carrier changes depending on a column size, a kind of a fixed carrier, etc. The amount of the fixed carrier is an amount as wet volume, preferably twice to 10,000 times, more preferably 5 to 500 times, the solids content of the raw material.

The raw material is passed through the column and then subjected to chromatography using water as an eluent to obtain a large number of fractions, and a fraction that absorbs light at a wavelength of 420 nm among the obtained fractions is isolated, whereby the extract of interest can be obtained. This method is sometimes referred to as ion chromatography separation. In the ion chromatography separation, each component is separated by a difference in a column passing rate caused by a difference in affinity between each component contained in the raw material and the ion exchange resin.

Liquid-passing conditions changes depending on composition of the raw material, a kind of a fixed carrier, etc. Degassed water is used as an eluent, and in the case of a single-column batch separation method, preferably, a flow rate is SV=0.3 to 1.0 hr$^{-1}$, an amount of a sample to be fed is 1 to 20% of the resin, and temperature is 40 to 70° C. When absorption at a wavelength of 420 nm, electrical conductivity (a measure of the salt content), and concentrations of sucrose, glucose, and fructose are analyzed for each of the fractions obtained by this separation method and represented as a time-series graph, peaks appear in the following order: a peak of light absorption at a wavelength of 420 nm, a peak of electrical conductivity, and peaks of sucrose and reducing sugar.

<α-Glucan Fraction>

Next, a method for producing the α-glucan fraction will be described.

Preferably, the ethanol-precipitated fraction is used for purification (production) of the α-glucan fraction. Hereinafter, a method for purifying the α-glucan fraction will be described taking the case of using the ethanol-precipitated fraction as an example.

First, the ethanol-precipitated fraction is passed through a column filled with an anion exchange resin as a carrier to adsorb components. As the anion exchange resin, a strong ion exchange resin is preferable. For example, a resin having a Q (quaternary ammonium) group or a QAE group can be used. Specific examples of a column provided with such a carrier can include Q-Sepharose Fast Flow (FF) and QAE-Sepharose FF. Preferably, such resin carriers are equilibrated with water in advance. For example, in the case of QAE-Sepharose FF, the resin is immersed in 2 M ammonium hydrogencarbonate to activate the QAE groups (a hydrogencarbonate ion that is a counterion is bound to the quaternary ammonium group covalently bound to Sepharose, i.e., converted into an $HCO_3^-$ form), then washed with water to remove remaining ammonium hydrogencarbonate, and subsequently suspended in water (equilibrated with water).

Next, an elution solvent is passed to elute the components adsorbed on the carrier in such a manner that the ionic strength of the elution solvent gradually increases. As the elution solvent, it is preferable to use an aqueous solution of an anionic salt, such as $NH_4HCO_3$, $HCOONH_4$, or NaCl.

The α-glucan fraction can be obtained from an eluted fraction obtained by elution with an elution solvent having a low ionic strength (Fraction A). As the elution solvent having a low ionic strength, for example, in the case where $HCO_3^-$ is used as the anion, an elution solvent having an anion concentration of 50 to 150 mM can be used, and the anion concentration is preferably 75 to 125 mM, more preferably 90 to 110 mM, and particularly preferably 100 mM.

The obtained eluted fraction (Fraction A) may be dialyzed using a dialysis membrane (e.g., Visking tube, MWCO: 12,000 to 14,000), followed by lyophilizing the non-dialysate, and then used in a subsequent step.

Next, the eluted fraction (Fraction A) is fractionated according to the molecular weight using a gel filtration column. For example, in the case where a gel filtration column having a molecular cutoff of $2 \times 10^3$ to $4 \times 10^5$ Da is used, the α-glucan fraction can be obtained from a fraction in an amount corresponding to void volume of first outflow (Vo fraction) (Fraction A1). As the gel filtration column having a molecular cutoff of about $2 \times 10^3$ to $4 \times 10^5$ Da, Sephacryl S-300, Superose 12, or the like can be used, for example. An elution pattern of the eluted fraction in the event of gel filtration may be created based on sugar, uronic acid, and UV absorption at 280 nm, and the fraction corresponding to the Vo fraction (Fraction A1) may be recovered for the α-glucan fraction. The obtained fraction (Fraction A1) may be further dialyzed by a usual method and subsequently lyophilized.

<Heteroglycan Fraction>

Next, a method for producing the heteroglycan fraction will be described.

Preferably, the ethanol-precipitated fraction is used for purification (production) of the heteroglycan fraction. Hereinafter, a method for purifying the heteroglycan fraction will be described taking the case of using the ethanol-precipitated fraction as an example.

First, the ethanol-precipitated fraction is passed through a column filled with an anion exchange resin as a carrier to adsorb components. As the anion exchange resin, a strong ion exchange resin is preferable. For example, a resin having a Q (quaternary ammonium) group or a QAE group can be used. Specific examples of a column provided with such a carrier can include Q-Sepharose Fast Flow (FF) and QAE-Sepharose FF. Preferably, such resin carriers are equilibrated with water in advance. For example, in the case of QAE-Sepharose FF, the resin is immersed in 2 M ammonium hydrogencarbonate to activate the QAE groups (a hydrogencarbonate ion that is a counterion is bound to the quaternary ammonium group covalently bound to Sepharose, i.e., converted into an $HCO_3^-$ form), then washed with water to remove remaining ammonium hydrogencarbonate, and subsequently suspended in water (equilibrated with water).

Next, an elution solvent is passed to elute the components adsorbed on the carrier in such a manner that the ionic strength of the elution solvent gradually increases. As the elution solvent, it is preferable to use a solution of an anionic salt, such as $NH_4HCO_3$, $HCOONH_4$, or NaCl.

The heteroglycan fraction can be obtained from an eluted fraction obtained by elution with an elution solvent having a high ionic strength. As the elution solvent having a high ionic strength, for example, in the case where $HCO_3^-$ is used as the anion, an elution solvent having an anion concentration of 200 to 2000 mM can be used. Preferably, the heteroglycan fraction is obtained by separately purifying an eluted fraction obtained by elution with a 250 to 350 mM elution solvent (Fraction B) and an eluted fraction obtained by elution with a 1600 to 2000 mM elution solvent (Fraction C), and subsequently combining Fractions B and C.

The obtained eluted fractions (Fraction B and Fraction C) may each be dialyzed using a dialysis membrane (e.g., Visking tube, MWCO: 12,000 to 14,000), followed by lyophilizing the dialysate, and then used in a subsequent step.

Next, the eluted fractions are fractionated according to the molecular weight using a gel filtration column. For example, in the case where a gel filtration column having a molecular cutoff of $1 \times 10^4$ to $1 \times 10^6$ Da is used, a fraction other than a fraction in an amount corresponding to the void volume of first outflow (Vo fraction) (Fraction B2) is recovered from Fraction B. For example, in the case where a gel filtration column having a molecular cutoff of $2 \times 10^3$ to $4 \times 10^5$ Da is used, a fraction in an amount corresponding to the void volume of first outflow (Vo fraction) (Fraction C1) is recovered from Fraction C. Elution patterns of the eluted fractions in the event of gel filtration may be created based on sugar, uronic acid, and UV absorption at 280 nm, and the fraction other than the Vo fraction (Fraction B2) from Fraction B and the fraction corresponding to the Vo fraction (Fraction C1) from Fraction C may be recovered.

As the gel filtration column having a molecular cutoff of about $1 \times 10^4$ to $1 \times 10^6$ Da, Sepharose CL-6B, Superose 6, or the like can be used, for example. In addition, as the gel filtration column having a molecular cutoff of about $2 \times 10^3$ to $4 \times 10^5$ Da, Sephacryl S-300, Superose 12, or the like can be used, for example.

The fractions obtained by gel filtration from Fraction B and Fraction C (Fraction B2 and Fraction C1), respectively, are combined, whereby the heteroglycan fraction can be obtained. The obtained heteroglycan fraction may be further dialyzed by a usual method and subsequently lyophilized.

[Peyer's Patch Activator]

A form of the Peyer's patch activator of the present invention is not particularly limited; however, the activator may be in a form of liquid or powder, or may be formed into a solid formulation or a liquid formulation using a carrier usually used for formulations. Methods for forming into such a formulation are known. The Peyer's patch activator thus obtained can be preserved in a form of liquid or powder. Particularly in the case of the form of liquid, the preservation is preferably refrigerated storage.

In the case where the Peyer's patch activator of the present invention is formed into a solid formulation, for example, dextrin, corn starch, or defatted rice bran may be added to the active ingredient polysaccharide to prepare the formulation. Methods for forming into such a formulation are known.

Timing of administration of the Peyer's patch activator of the present invention is not particularly limited. A dosage of the Peyer's patch activator of the present invention varies depending on a formulation form, a kind, health conditions, age or degree of growth of a target human or non-human animal, etc., and thus is not particularly limited. For example, 1 to 1,000 mg in terms of the active ingredient polysaccharide may be administered per kg of body weight per day.

A dosage form of the Peyer's patch activator of the present invention is not particularly limited; however the activator may be administered orally, enterally, or transnasally, for example. In addition, the activator can also be administered in a form that is easily retained in the oral cavity (including chewing gum, etc.).

The Peyer's patch activator of the present invention has a Peyer's patch activating effect, and thus can also be used as an intestinal immune enhancer, an intestinal immunity modifier, an intestinal infection ameliorating agent, an inflammation ameliorating agent, a virus infection ameliorating agent, a bacterial infection ameliorating agent, etc., for example. In particular, through its intestinal immunity enhancing effect, the activator can also be used as a preventive/therapeutic agent for *plasmodium* infection, for example.

[Medicine for Preventing or Treating *Plasmodium* Infection]

The Peyer's patch activator of the present invention can prevent or treat *plasmodium* infection through the intestinal immunity enhancing effect. Therefore, the present invention can provide a medicine for preventing or treating *plasmodium* infection containing the Peyer's patch activator as an active ingredient.

Combined effects are obtained by using the medicine for preventing or treating *plasmodium* infection in combination with an existing antimalarial agent. Therefore, the medicine may be used so as to be used in combination with an existing antimalarial agent.

Examples of antimalarial agents include quinine (a compound represented by the following formula (1)), mefloquine (a compound represented by the following formula (2)), sulfadoxine (a compound represented by the following formula (3)), pyrimethamine (a compound represented by the following formula (4)), chloroquine (a compound represented by the following formula (5)), primaquine (a compound represented by the following formula (6)), artesunate (a compound represented by the following formula (7)), artemether (a compound represented by the following formula (8)), and lumefantrine (a compound represented by the following formula (9)). These antimalarial agents can be used alone or in combination of two or more thereof.

[Chemical Formula 1]

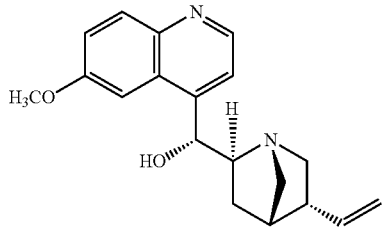

(1)

[Chemical Formula 2]

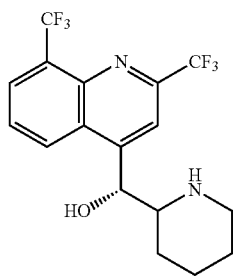

(2)

[Chemical Formula 3]

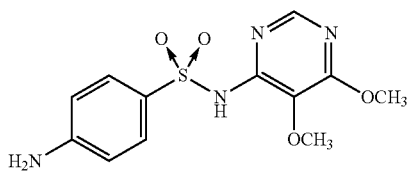

(3)

[Chemical Formula 4]

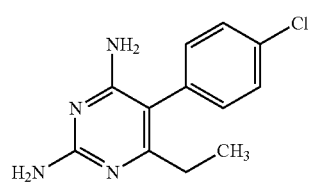

(4)

[Chemical Formula 5]

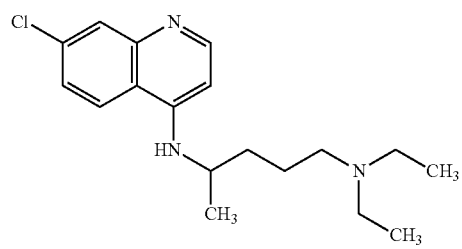

(5)

[Chemical Formula 6]

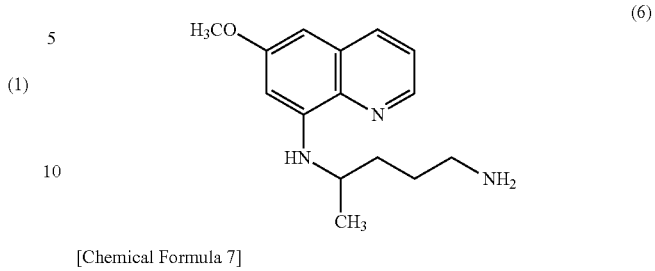

(6)

[Chemical Formula 7]

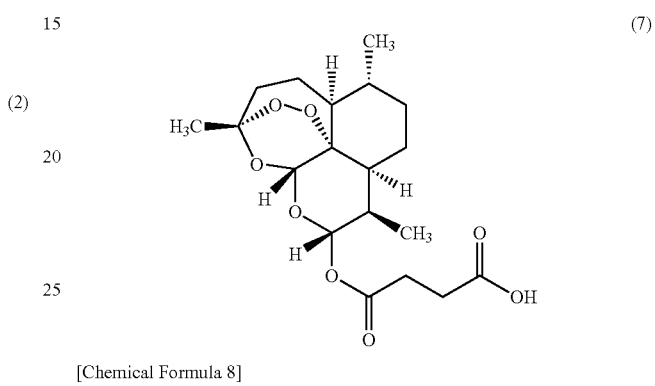

(7)

[Chemical Formula 8]

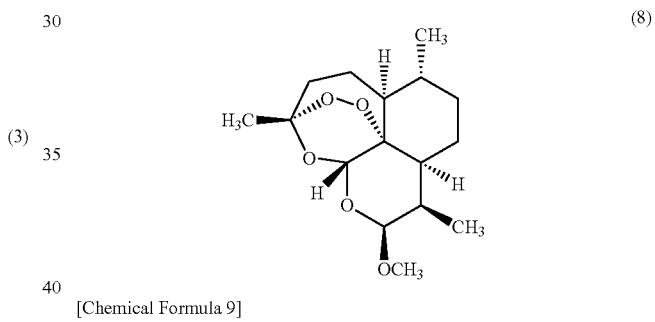

(8)

[Chemical Formula 9]

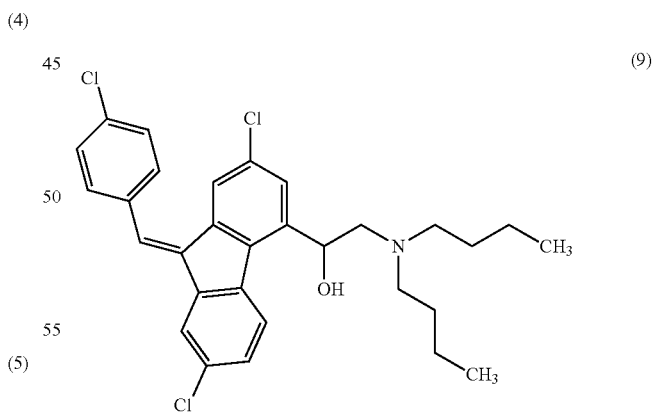

(9)

It is preferable to contain artesunate as the antimalarial agent, because the combined effect with the medicine for preventing or treating *plasmodium* infection of the present invention is high. In addition, the medicine for preventing or treating *plasmodium* infection of the present invention is more preferably used so as to be used in combination with artesunate.

EXAMPLES

Hereinafter, the present invention will be described in further detail based on examples. However, the present invention is not limited to these examples.

Test Example 1: Test of Peyer's Patch Activating Effect of Ethanol-Precipitated Fraction of Extract Derived from Sugar Cane <Production of Extract Derived from Sugar Cane>

(Fractionation of Second Molasses by Single-Column Batch Separation Using Ion Exchange Resin)

Using a second-molasses treated liquid obtained in a raw sugar factory as a raw material, fractionation separation by ion exchange column chromatography was performed by a single-column batch separation method using an FPLC system (manufactured by Pharmacia Corporation). The second-molasses treated liquid used as a raw material is one obtained by diluting a second molasses, followed by purification with sodium carbonate and filtration with diatom earth. The raw material liquid was analyzed to have the following values: Brix (Bx): 47.4, sugar content (Pol.): 23.2, sugar purity (Purity): 48.9, reducing sugar content: 3.2%.

A column was filled with 500 ml of a gel-type strongly acidic cation exchange resin (trade name: UBK530, sodium-ion type, Mitsubishi Chemical Corporation). The column had an inner diameter of 26 mm and a height of 1000 mm and was provided with a flow adapter. Liquid-passing conditions were as follows: using degassed distilled water as an eluate, the liquid was passed at a flow rate of $SV=0.5\ hr^{-1}$ (4.17 ml/min) at a temperature of 60° C.

About 25 ml of the raw material was fed to the ion exchange column. Fractionation conditions were as follows: the eluate was started being recovered 30 minutes after the feeding of the raw material, and recovered for 3.6 minutes per test tube (about 15 ml/test tube) and recovered in 30 test tubes in total.

Figure 6:
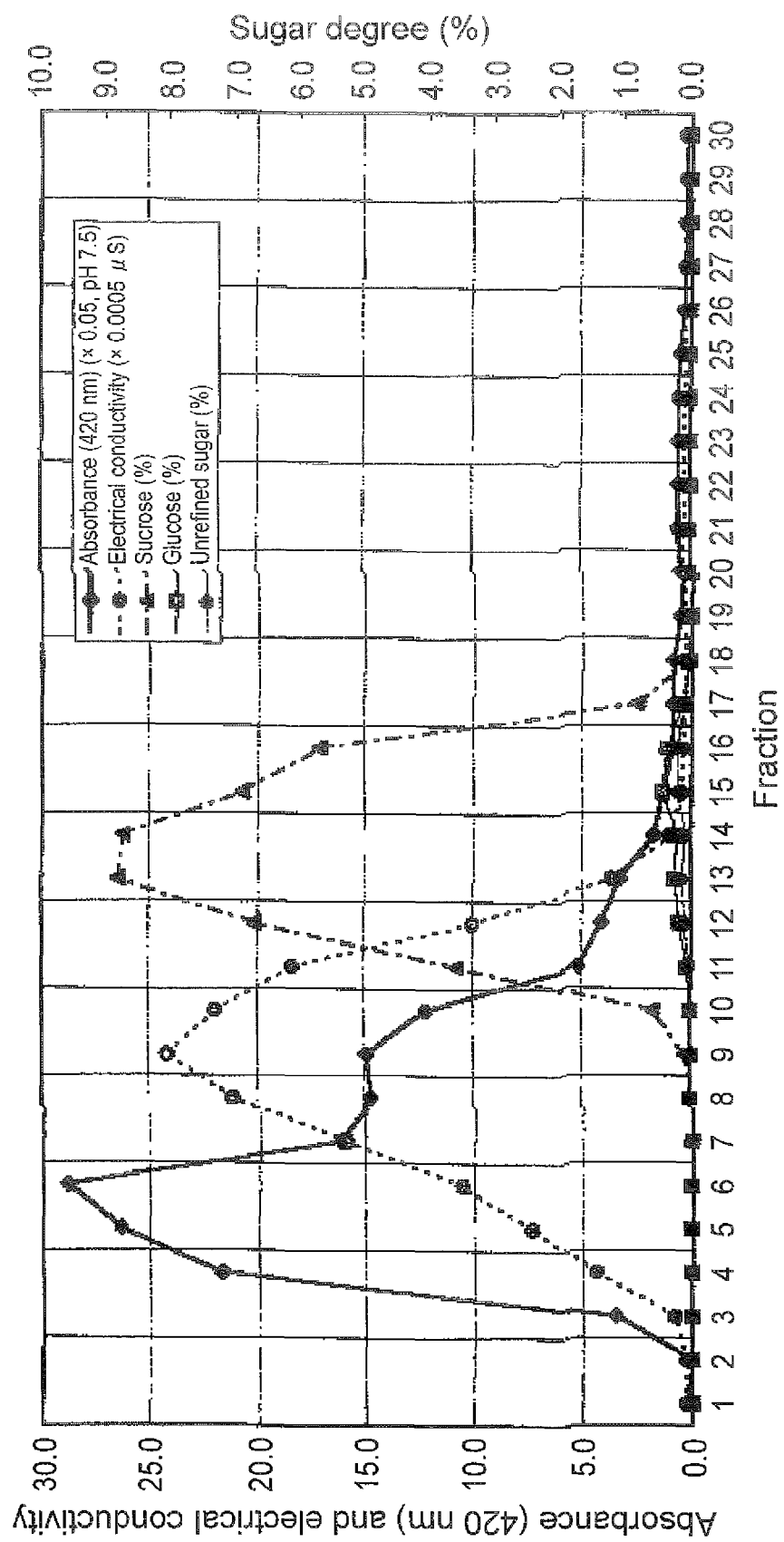
FIG. 6 is a graph showing an elution pattern in column chromatography performed in Production Example 1.

Absorbance at a wavelength of 420 nm, electrical conductivity, and sugar (Sucrose, Glc, Fru) contents (mass % based on the total solids mass of all fractions) were measured for each of the obtained 30 fractions (Fractions 1 to 30), and the results are shown in FIG. 6. Here, in the measurement of absorbance, 0.1 ml of each fraction was added to 2 ml of a 0.5 mM phosphate buffer (pH 7.5) and used as a measurement sample. In the measurement of electrical conductivity, each fraction was diluted with distilled water to 0.5% and used as a measurement sample. The sugar contents were measured by a usual method using HPLC.

The obtained 30 fractions were collected as follows to obtain Samples 1 to 8.
Sample 1: Fractions 3 and 4.
Sample 2: Fractions 5 and 6.
Sample 3: Fractions 7 and 8.
Sample 4: Fractions 9 and 10.
Sample 5: Fractions 11 and 12.
Sample 6: Fractions 13 and 14.
Sample 7: Fractions 15 and 16.
Sample 8: Fractions 17 to 30.

Incidentally, Fractions 1 and 2 had no component to be eluted, and thus were discarded.

Each sample was lyophilized overnight into a powder. 0.25 g of the obtained lyophilized powder was dissolved in a 0.5 mM phosphate buffer (pH 7.5) to make 100 ml, and absorbance at a wavelength of 420 nm was measured. The results are shown in Table 1 below. The absorbance of Sample 8 was as relatively high as 0.86, and this is because the sample is a collection of tailing components. While other samples are each composed of two fractions, Sample 8 is a collection of 14 fractions. Therefore, although the absorbance at 420 nm is high, it is inefficient to recover these fractions.

Results of the analysis of each sample are shown in the following Table 1. An electrical conductivity-ash content in Table 1 was calculated from a coefficient determined from a calibration curve of the relation between electrical conductivity and known sulfated ash. In Table 1, distribution of lyophilized solids is a proportion (%) of solids mass of each sample relative to the total solids mass of all the samples. The electrical conductivity-ash content and the content of each sugar (Sucrose, Glc, Fru) are each a proportion (mass %) relative to the solids mass of each sample. From the content of each sugar (Sucrose, Glc, Fru), it is understood that Samples 1 to 3 correspond to non-sugar fractions, and Samples 4 to 8 are sugar fractions. "Sugar" here refers to monosaccharides and sucrose.

TABLE 1

Analysis of Second-Syrup Samples Fractionated by Ion Exchange Resin

| | Distribution of lyophilized solids (%) | Electrical conductivity-ash content (%) | Sucrose content (%) | Glc content (%) | Fru content (%) | Absorbance |
|---|---|---|---|---|---|---|
| Sample 1 | 3.1 | 32.9 | 0 | 0 | 0 | 2.72 |
| Sample 2 | 7.2 | 39.7 | 0 | 0 | 0 | 2.01 |
| Sample 3 | 10.7 | 51.4 | 10.4 | 0 | 0 | 0.83 |
| Sample 4 | 21.9 | 32.6 | 45.6 | 1.4 | 0.7 | 0.33 |
| Sample 5 | 25.9 | 18.8 | 64.2 | 2.9 | 1.3 | 0.16 |
| Sample 6 | 19.6 | 10 | 73.5 | 4.7 | 2.3 | 0.11 |
| Sample 7 | 8.4 | 3.5 | 74 | 6.2 | 3.2 | 0.14 |
| Sample 8 | 3.1 | 3.3 | 29.8 | 4.5 | 4.4 | 0.86 |
| Ion chromatography separation liquid | — | 43.7 | 5.9 | 0.9 | 1.4 | 1.04 |

(Separation by Simulated Moving Bed Column Chromatography using Ion Exchange Resin)

Using as a raw material a second-molasses that is obtained in a raw sugar factory by recovering sucrose crystals twice in a crystallization can and removing crystals by centrifugation, ion exchange column chromatography separation was performed by a simulated moving bed continuous separation method using a separation column filled with a cation exchange resin.

Steps from the preparation of the raw material to the ion exchange chromatography separation are performed continuously, and thus a solids concentration or composition of the liquid in each step slightly varies with time; however the following concentration and composition are values measured in the steady operation.

The second molasses had a Brix (Bx.) of about 85. This concentration is too high for column chromatography treatment, and thus the second molasses was diluted to a Brix of about 50. Slaked lime and sodium carbonate were added thereto to aggregate impurities, followed by filtration with diatom earth. The obtained filtrate had a Brix of 47.3, a sugar content (Pol.) of 23.6, a sugar purity (Purity) of 49.9, and a reducing sugar content of 2.5%. The filtrate was used as a raw material for ion exchange chromatography.

Ion exchange chromatography was performed by a simulated moving bed continuous separation method using UBK530 (Mitsubishi Chemical Corporation) as a cation exchange resin. A resin-filled separation column is divided into eight parts, and a resin amount per column is 6.5 m$^3$. Feeding of the raw material liquid and an eluent (water) and positions of extracting a sucrose fraction and a non-sucrose fraction were switched every fixed time, whereby feeding and extraction were continuously performed. Preset values in a steady state were as follows: feeding flow rate: 3 m$^3$/hour, eluent water flow rate: 13.5 m$^3$/hour, non-sucrose fraction extraction flow rate: 12.13 m$^3$/hour, sucrose fraction extraction flow rate: 4.37 m$^3$/hour, switching time: 267 seconds. As a result of this chromatography treatment, a sucrose fraction and a non-sucrose fraction were separated. These correspond to Fractions 10 to 17 (sucrose fraction) and a collection of Fractions 1 to 9 and Fractions 18 to 30 (non-sucrose fraction) in FIG. 6, respectively. In the sucrose fraction, sucrose was about 87% of the solids content (based on HPLC analysis) and the Brix was about 35. This fraction was mixed with a purified juice, returned to the step, and subjected again to the sucrose recovery operation. In addition, the obtained non-sucrose fraction had a sucrose content of about 0.3% (based on HPLC analysis) and a Brix of about 8. This non-sucrose fraction was concentrated in a concentration can to have a Brix of 40.0, a sugar content (Pol.) of 2.3, a sugar purity (Purity) of 5.8, and a reducing sugar content of 5.4%. This non-sucrose fraction was used as an extract derived from sugar cane. The extract derived from sugar cane was lyophilized overnight to be used in a later test. 0.25 g of the obtained lyophilized powder was dissolved in a 0.5 mM phosphate buffer (pH 7.5) to make a 100 ml solution, and absorbance at a wavelength of 420 nm was measured. The absorbance was 1.11.

<Preparation of Ethanol-Precipitated Fraction>

Purified water was added to the extract derived from sugar cane (lyophilized weight: 418.57974 g) to make a total amount of 500 mL, a four-fold amount of ethanol was added with stirring, and the mixture was stirred at room temperature overnight. Centrifugation (6,000 rpm, 4° C., 30 minutes) was performed, followed by dialysis of the obtained precipitate with running water and purified water (7 days) and lyophilization of the non-dialyzed fraction to obtain an ethanol-precipitated fraction (also referred to as "SCE-4") (yielded amount: 20.11 g, yield: 4.8%/a).

<Preparation of Saccharide-Chain-Degraded SCE-4>

The ethanol-precipitated fraction (SCE-4) (50.45 mg) was dissolved in a 50 mM acetate buffer (pH 4.5, 30 mL), and subsequently a 50 mM acetate buffer (10 mL) containing 100 mM NaIO$_4$ was added at 4° C., followed by stirring for 96 hours in a dark place and periodate oxidation. Ethylene glycol (1 mL) was added to the reaction solution and stirred at room temperature for 1 hour to decompose excess NaIO$_4$. Then, the reaction mixture was dialyzed for 2 days using purified water, and the non-dialysate was concentrated under reduced pressure. Further, NaBH$_4$ (180 mg) was added and stirred at room temperature for 12 hours, and acetic acid was added dropwise to cause neutralization. The reaction liquid was further dialyzed for 3 days using purified water, and subsequently the non-dialysate was lyophilized to obtain a periodate oxide (saccharide-chain-degraded SCE-4) (yielded amount: 31.99 mg, yield: 62.76%).

<Preparation of Delignified SCE-4>

The ethanol-precipitated fraction (SCE-4) (50.59 mg) was dissolved in a 4% aqueous solution of acetic acid (50 mL), and subsequently NaClO$_2$ (250 mg) was added, followed by stirring for 40 minutes in a water bath at 70° C. The reaction liquid was neutralized using 3 M NaOH with ice cooling. The reaction liquid was dialyzed with running water overnight and subsequently dialyzed for 4 days using purified water, and the non-dialysate was lyophilized to obtain a delignified polysaccharide fraction (delignified SCE-4) (yielded amount: 22.39 mg, yield: 44.14%).

<Preparation and Culture of Mouse Peyer's Patch Cells>

A C3H/HeJ mouse was euthanized with isoflurane (Escain inhalational anesthetic, Mylan Pharmaceuticals), and subsequently Peyer's patches were taken out from the small intestine using scissors for ophthalmology. These Peyer's patches were placed in a sterilized petri dish supplemented with an ice-cooled RPMI 1640 culture medium (2 mL) containing ice-cooled 5% fetal bovine serum (FBS), and crushed on a stainless steel mesh (200 meshes) using a rubber part of an inner cylinder of a 5 mL disposable injection syringe, whereby the Peyer's patch cells were released. The cell suspension was transferred to a 50 mL Falcon tube and stirred in a vortex mixer for a short period of time. The cell suspension was filtered through a stainless steel mesh (150 meshes) and subsequently centrifuged (1,500 rpm, 4° C., 7 minutes), and the culture medium was decanted to obtain the Peyer's patch cells. The cells were washed by repeating the same procedure four times in total using an FBS-containing RPMI 1640 culture medium (10 mL), and subsequently filtered through a stainless steel mesh (200 meshes). Using this cell suspension (20 µL), the number of the cells was counted by a cell counter, and subsequently a Peyer's patch cell suspension having 1 to 2×10$^6$ cells/mL was prepared using an FBS-containing RPMI 1640 culture medium.

To a 96-well culture plate (3072, FALCON), the Peyer's patch cell suspension (180 µL/well) and a polysaccharide sample solution (20 µL/well, final polysaccharide concentration: 100 µg/mL, 50 µg/mL, 10 µg/mL) were added, and culture was performed at 37° C. for 2 to 6 days in 5% CO$_2$ and 95% air. The culture supernatant was transferred to another 96-well culture plate and preserved at −20° C. until use. A culture supernatant obtained by adding an injection solvent (20 µL/well) in place of the polysaccharide solution and performing culture was used as a control.

<Preparation of Mouse Bone Marrow Cells>

After a C3H/HeJ mouse (7-week old, female) was euthanized with isoflurane, the thighbone was excised, and using a 5 mL injection syringe equipped with a 23 G injection needle, bone marrow cells were pushed out from the thighbone with an FBS-containing RPMI 1640 culture medium (5 mL) and thus collected. The bone marrow cells were dispersed in a vortex mixer, subsequently filtered through a stainless steel mesh (200 meshes), and then centrifuged (1,200 rpm, 4° C., 7 minutes) to recover bone marrow cells. After the same procedure was repeated three times to wash the cells, the bone marrow cells were suspended in an FBS-containing RPMI 1640 culture medium (10 mL), the number of the cells was counted by a cell counter, and subsequently, a bone marrow cell suspension ($5 \times 10^5$ cells/mL) was prepared using an FBS-containing RPMI 1640 culture medium.

<Peyer's Patch Activating Effect Test>

To a 96-well culture plate, the Peyer's patch cell culture supernatant (50 μL/well), the bone marrow cell suspension ($5 \times 10^5$ cells/mL, 100 μL/well), and an FBS-containing RPMI 1640 culture medium (50 μL/well) were added, and culture was performed at 37° C. for 6 days in 5% $CO_2$ and 95% air. After Alamer Blue (20 μL/well, Biosource) was added to the cultured bone marrow cell suspension and culture was performed at 37° C. for 6 to 24 hours in 5% $CO_2$ and 95% air, an amount of the resulting fluorescent substance was measured by a fluorescent plate reader (Infinite M200, Tecan, excitation wavelength; 544 nm, measurement wavelength; 590 nm), and the number of the grown bone marrow cells as the obtained relative fluorescence intensity was taken as a bone marrow cell growth promoting factor amount.

<Statistical Test>

All results in the examples are shown as an average±S.D. Statistically significant differences between the control and the test samples were tested by Fisher's PLSD after ANOVA test.

<Results>

FIG. 1 shows results of the Peyer's patch activating effect test. The bone marrow cell growth promoting factor amount is shown as the Peyer's patch activating effect. In the ethanol-precipitated fraction (SCE-4), the Peyer's patch activating effect was observed. Meanwhile, in the case where the saccharide chain of SCE-4 was degraded (saccharide-chain-degraded SCE-4), the activity decreased significantly to such a level that there is no significant difference from the control. In addition, in the case where SCE-4 was delignified (delignified SCE-4), the activity was observed. These results suggested that a substance having the Peyer's patch activating effect is contained in the polysaccharide-containing component of the ethanol-precipitated fraction (SCE-4) in the extract derived from sugar cane.

Production Example 1: Preparation of α-Glucan Fraction and Heteroglycan Fraction <Preparation of Ethanol-Precipitated Fraction>

An extract derived from sugar cane was obtained in the same manner as in Test Example 1. Purified water was added to the extract derived from sugar cane (lyophilized weight: 418.57974 g) to make a total amount of 500 mL, a four-fold amount of ethanol was added with stirring, and the mixture was stirred at room temperature overnight. Centrifugation (6,000 rpm, 4° C., 30 minutes) was performed, followed by dialysis of the obtained precipitate with running water and purified water (7 days) and lyophilization of the non-dialyzed fraction to obtain a brownish red ethanol-precipitated fraction (SCE-4) (yielded amount: 20.11 g, yield: 4.8%).

<Preparation of α-Glucan Fraction and Heteroglycan Fraction>

Figure 2:
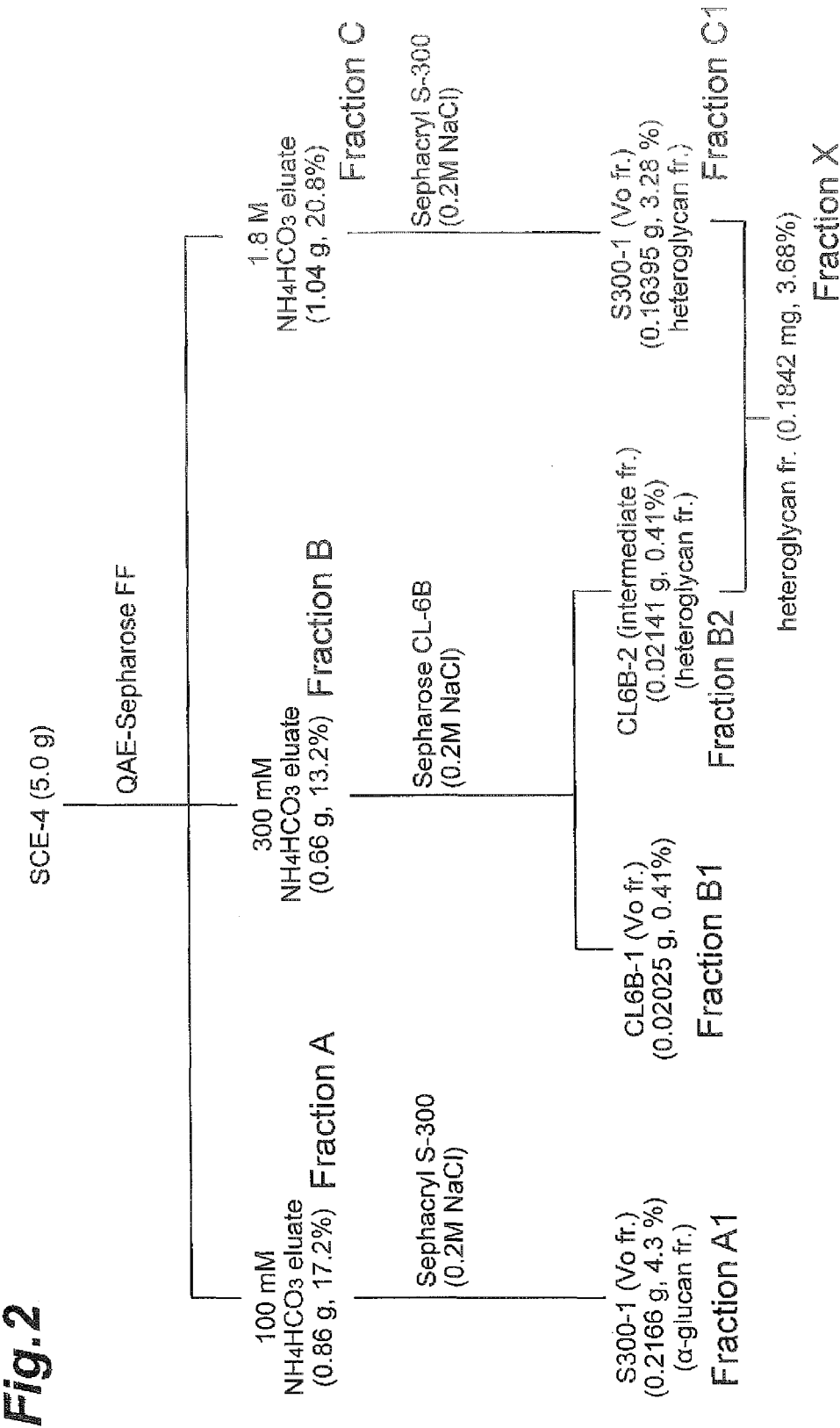
FIG. 2 is a scheme showing a polysaccharide fraction separation step in Production Example 1.

An α-glucan fraction ("Fraction A1" in FIG. 2) and a heteroglycan fraction ("Fraction X" in FIG. 2) were prepared from the ethanol-precipitated fraction (SCE-4) in accordance with a scheme shown in FIG. 2.

SCE-4 (5.0 g) was added to and passed through QAE-Sepharose FF (5.5 i.d.×26 cm), and subsequently, the adsorbed components were gradually eluted using sequentially 100 mM $NH_4HCO_3$ (6 L), 300 mM $NH_4HCO_3$ (10 L), and 1.8 M $NH_4HCO_3$ (10 L). The fractionated fractions were dialyzed using a dialysis membrane (Visking tube, MWCO: 12,000 to 14,000), and subsequently the non-dialysate was lyophilized to obtain fractionated fractions (Fraction A, Fraction B, and Fraction C).

Fraction A (fraction eluted with 100 mM $NH_4HCO_3$): 0.86 g, 17.2%

Fraction B (fraction eluted with 300 mM $NH_4HCO_3$): 0.66 g, 13.2%.

Fraction C (fraction eluted with 1.8 M $NH_4HCO_3$): 1.04 g, 20.8%.

(α-Glucan Fraction)

Fraction A was added to Sephacryl S-300 (2.6 i.d.×90 cm) equilibrated with a 0.2 M NaCl solution, and subsequently eluted with 0.2 M NaCl. In accordance with an elution pattern of the eluted fraction created based on the relative sugar content, relative uronic acid content, and UV absorption at 280 nm measured by a usual method, fractionated fractions were recovered. A Vo eluted fraction was obtained as an α-glucan fraction ("Fraction A1" in FIG. 2) in the form of a white lyophilized powder (yielded amount: 0.2166 g, yield: 4.3%).

(Heteroglycan Fraction)

Fraction B was fractionated through Sepharose CL-6B (2.6 i.d.×90 cm) equilibrated with a 0.2 M NaCl solution to obtain an intermediate fraction ("Fraction B2" in FIG. 2) (yielded amount: 0.02141 g, yield: 0.41%).

Meanwhile, Fraction C was fractionated through Sephacryl S-300 (2.6 i.d.×90 cm) equilibrated with 0.2 M NaCl to obtain a Vo eluted fraction ("Fraction C1" in FIG. 2) (yielded amount: 0.16395 g, yield: 3.28%).

Fraction B2 and Fraction C1 were combined to obtain a heteroglycan fraction in the form of a white lyophilized powder ("Fraction X" in FIG. 2) (yielded amount: 0.1842 g, yield: 3.68%).

Test Example 2: Analysis of α-Glucan Fraction and Heteroglycan Fraction

<Measurement of Molecular Weight Distribution>

Molecular weight distribution of the test samples (the α-glucan fraction and the heteroglycan fraction) was analyzed by high-speed gel filtration chromatography (HPSEC) using a coupled column of Asahipak GS710 and Asahi-pak GS620 (each 0.76 i.d.×60 cm) (Showa Denko). The molecular weight was calculated from retention time of a test sample based on a calibration curve of molecular weight/retention time coefficient (Kay) created from retention time of a standard polysaccharide (pullulan P-800, 400, 200, 100, 50, 20, 10 and 5, Showa Denko) in HPSEC.

HPSEC conditions are as follows.

Pump system; JASCO PV-980 (Jasco)

Detector, Shodex RI SE-62 (Showa Denko) (sensitivity: ×2)

Eluent; 0.2 M NaCl (1.0 mL/min)

<Colorimetry>

A total sugar amount, an amount of uronic acid, and an amount of a protein were measured by the phenol-$H_2SO_4$ method, the m-hydroxybiphenyl method, and the Bradford method, respectively. As authentic samples, Glc was used for the phenol $H_2SO_4$ method, GalA for the m-hydroxybiphenyl method, and bovine gammaglobulin (Bio-Rad) for the Bradford method.

<Analysis of Component Sugars>

The component sugars were analyzed by the TMS methyl glycoside method.

A standard mixture of monosaccharides (Glc, Gal, GlcA, GalA, Ara, Fuc, Xyl, Man, and Rha, 5 μg each) and test samples (50 to 100 μg each) were each transferred in a 13-mm screw-cap test tube, further a myo-inositol solution (internal standard: 20 μL, 1 mg/mL) was added, and subsequently the solvent was completely distilled off under reduced pressure. A 1 M HCl-MeOH solution (100 to 300 μL, Wako Pure Chemical Industries) was added to each test tube and subjected to methanolysis under hermetically sealed conditions (80° C., 15 hours). Tert-BuOH (5 μL) was added to the reaction solution, and the solvent was distilled off in a nitrogen gas stream (40° C.), followed by addition of a Tri-Sil reagent (100 μL, Pierce) and reaction under hermetically sealed conditions (80° C., 20 minutes). The reagent was distilled off in a nitrogen gas stream (40° C.), subsequently hexane (2 mL) was added to the reaction product, and the mixture was ultrasonically treated for a few seconds to extract a TMS derivative. Insoluble materials in the extract were removed by centrifugation (2,000 rpm, 4° C., 5 minutes), subsequently the solvent was distilled off in a nitrogen gas stream (40° C.), and the obtained hexane solution of the TMS derivative was analyzed by gas chromatography (GLC). Each monosaccharide derivative was identified by comparison with retention time of a standard derivative, and a proportion (mol. %) was calculated from peak area and a response factor to an FID detector of each monosaccharide derivative obtained in each experiment.

GLC conditions are as follows.

Instrument; HP5890 Series II gas chromatograph (Hewlett Packard)

Column; DB-1 capillary column (0.25 mm i.d.×30 m, liquid membrane thickness: 0.25 μm, J&W Scientific Inc.)

Carrier gas; He (total flow rate; 80 mL/min, column inlet pressure; 21 psi, gas purity; 99.9999%)

Inlet temperature; 250° C.

Detector temperature; 280° C.

Oven temperature program; 60° C. (1 minute), 60° C.→170° C. (30° C./min), 170° C.→190° C. (1° C./min), 190° C.→300° C. (30° C./min), 300° C. (5 minutes)

<Methylation Analysis>

Methylation analysis for analysis of sugar linkage pattern was performed in accordance with the following method modified from the Hakomori method and the method of Waeghe et al.

(Methylation of Polysaccharide using Sodium Methylsulfinyl Carbanion)

After a test sample (500 μg) was placed in a screw-cap test tube (15 i.d.×100 mm) and dried under reduced pressure in a desiccator overnight, anhydrous dimethyl sulfoxide (dry DMSO, Sigma) was added and the mixture was ultrasonically treated in a nitrogen gas stream under hermetically sealed conditions for 15 minutes and warmed at 50 to 60° C. until the sample was completely dissolved (a few hours to one whole day and night). Sodium methylsulfinyl carbanion (500 μL) was added to the sample solution and ultrasonically treated for 1 hour in a nitrogen gas stream, and subsequently the mixture was allowed to react for 3 hours at room temperature. After the reaction, using a small amount of the reaction liquid (5 to 10 μL), whether excess sodium methylsulfinyl carbanion remained was confirmed with a triphenylmethane reagent (Wako Pure Chemical Industries). In the case where sodium methylsulfinyl carbanion was insufficient, sodium methylsulfinyl carbanion was further added, and the above-mentioned operation was repeated until an excess of sodium methylsulfinyl carbanion remained. The reaction mixture was frozen, and subsequently $CH_3I$ (iodomethane, Yanagishima Pharmaceuticals Co., Ltd., special grade, 1 mL) was added, and the mixture was ultrasonically treated in a nitrogen gas stream under hermetically sealed conditions for 15 minutes and allowed to react at room temperature for 4 hours or more. After the completion of the reaction, $CH_3I$ in the reaction liquid was distilled off under reduced pressure and frozen with ice cooling, and purified water in an amount equivalent to the total amount of DMSO and methylsulfinyl carbanion used was added to decompose the remaining methylsulfinyl carbanion and halt the reaction. Further, saturated $Na_2S_2O_3$ (from about 250 μL) was added to the reaction liquid until the yellow color of the liquid disappeared.

(Recovery of Fully Methylated Polysaccharide)

Sep-pak C18 cartridge (1 mL, Waters Associate Inc.) was washed using distilled ethanol (10 mL×4) and then water (2 mL×3), and subsequently, the methylation reaction mixture was passed through the cartridge to adsorb the methylated polysaccharide onto the cartridge. The cartridge was washed with 50% DMSO (2 mL×5) and then with water (2 mL×5), and subsequently, the methylated polysaccharide was eluted using distilled ethanol (2 mL×3) and subsequently the solvent was distilled off under reduced pressure to obtain a fully methylated polysaccharide.

(Reduction of Carboxyl Group of Uronic Acid in Methylated Polysaccharide)

Carboxyl groups of uronic acid residues in the fully methylated polysaccharide were reduced to a deuterated primary alcohol by the following method. That is, the fully methylated polysaccharide sample was dissolved in 95% ethanol (0.21 mL) and tetrahydrofuran (THF, 0.51 mL), and subsequently sodium borodeuteride ($NaBD_4$, 1.8 mg) was added and mixed, followed by reaction for 18 hours or more at room temperature and further warming at 70° C. for 1 hour to reduce carboxymethyl groups. The reaction liquid was neutralized using acetic acid, and 7 to 8 drops of acetic acid were further added to halt the reaction. The reaction solution was dried and hardened under reduced pressure, and subsequently, in order to remove the produced boric acid, the operation of adding distilled methanol (1 mL) to the reaction product and distilling off the solvent from the product under reduced pressure was repeated at least four times. After dissolving the product with a 50% DMSO solution, a carboxyl-reduced fully methylated polysaccharide was recovered in the same manner as the method described in (Recovery of Fully Methylated Polysaccharide).

(Derivatization from Fully Methylated Polysaccharide to Partially Methylated Alditol Acetate Compound, and Analysis)

The obtained carboxyl-reduced fully methylated polysaccharide was heated at 121° C. for 1 hour under hermetically sealed conditions in a screw-cap test tube (15 i.d.×100 mm) using 2 M trifluoroacetic acid (TFA, 1 mL) to cause hydrolysis. After the completion of the reaction, the reaction solution cooled to room temperature was dried and hardened under reduced pressure and further dried under reduced pressure for 30 minutes in a desiccator to remove the remaining TFA. The obtained hydrolysate was dissolved in 95% ethanol (distilled, 1 mL), and 7 to 8 drops of 25% aqueous ammonia were added to make it ammonia alkaline, followed by addition of excess sodium borohydride (NaBH$_4$) and reaction at room temperature for 4 hours or more. An acetic acid solution was added dropwise to the reaction liquid to decompose the remaining NaBH$_4$, subsequently, 7 to 8 drops were further added, and the solvent was distilled off by drying and hardening under reduced pressure. Methanol (1 mL) was added to the reaction product and the operation of distilling off the solvent under reduced pressure was repeated four times to remove the produced boric acid. The reaction product was dried under reduced pressure in a desiccator for 1 hour, and subsequently, acetic anhydride was added, and the mixture was heated and allowed to react at 121° C. for 3 hours under hermetically sealed conditions to cause acetylation. The reaction solution was allowed to stand to room temperature, subsequently, toluene (1 mL) was added and mixed, and acetic anhydride was removed at 40° C. in an air stream. Water (1 mL) and CHCl$_3$ (2 mL) were added to the reaction product for liquid-liquid partition, followed by centrifugation (4° C., 2,500 rpm, 5 minutes), and subsequently the upper aqueous layer was removed by suction. Further, the CHCl$_3$ layer was washed four to five times using water (1 mL), and subsequently CHCl$_3$ was distilled off under reduced pressure to obtain a partially methylated alditol acetate derivative. The derivative was analyzed by gas chromatography (GLC) and gas chromatography/mass spectrometry (GLC-MS) under the following conditions. Methylated alditol acetate was identified by comparison with an authentic fragment ion sample and comparison with retention time relative to 2,3,4,6-tetra-OMe-1,5-di-OAc-galactitol. Molar proportions of the methylated sugars (mol. %) were each determined by peak area and a response factor to FID.

GLC:

Instrument; HP5890 Series II gas chromatograph (Hewlett Packard)

Capillary column; SP-2380 capillary column (0.25 mm i.d.×30 m, liquid membrane thickness: 0.25 μm, SPELCO/ALDRICH) Carrier gas; He (total flow rate; 80 mL/min, column inlet pressure; 10 psi, gas purity; 99.9999%)

Injector temperature; 250° C.

Detector temperature; 250° C.

Oven temperature; 60° C. (1 min), 60° C.→150° C. (30° C./min), 150° C.→250° C. (1.5° C./min), 250° C. (1 min)

MS:

Mass spectrometer, HP5970 B Mass Selective Detector (70 eV, 280° C.)

<Results>

Figure 7:
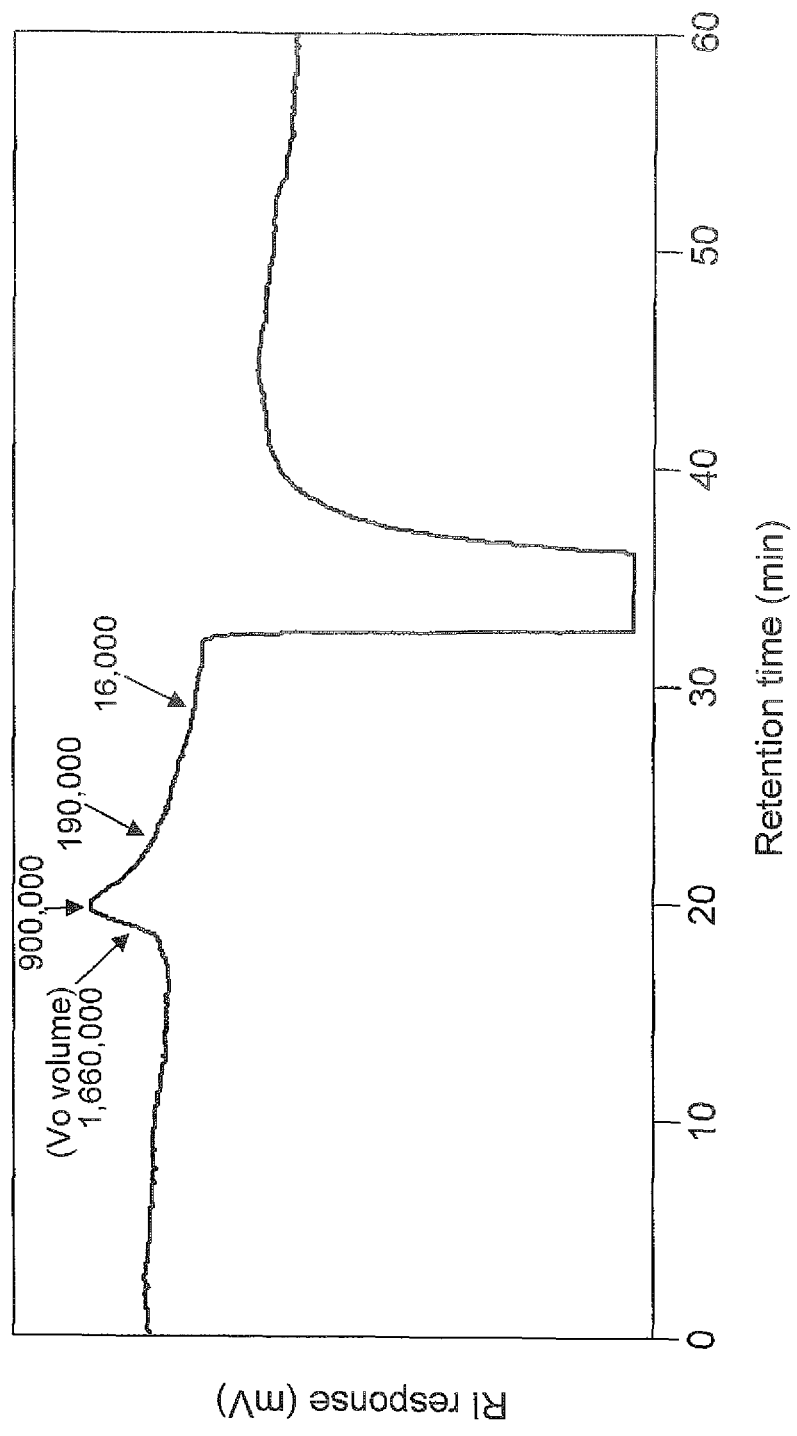
FIG. 7 is an HPSEC chart showing a molecular weight distribution of an α-glucan fraction in Test Example 2.
Figure 8:
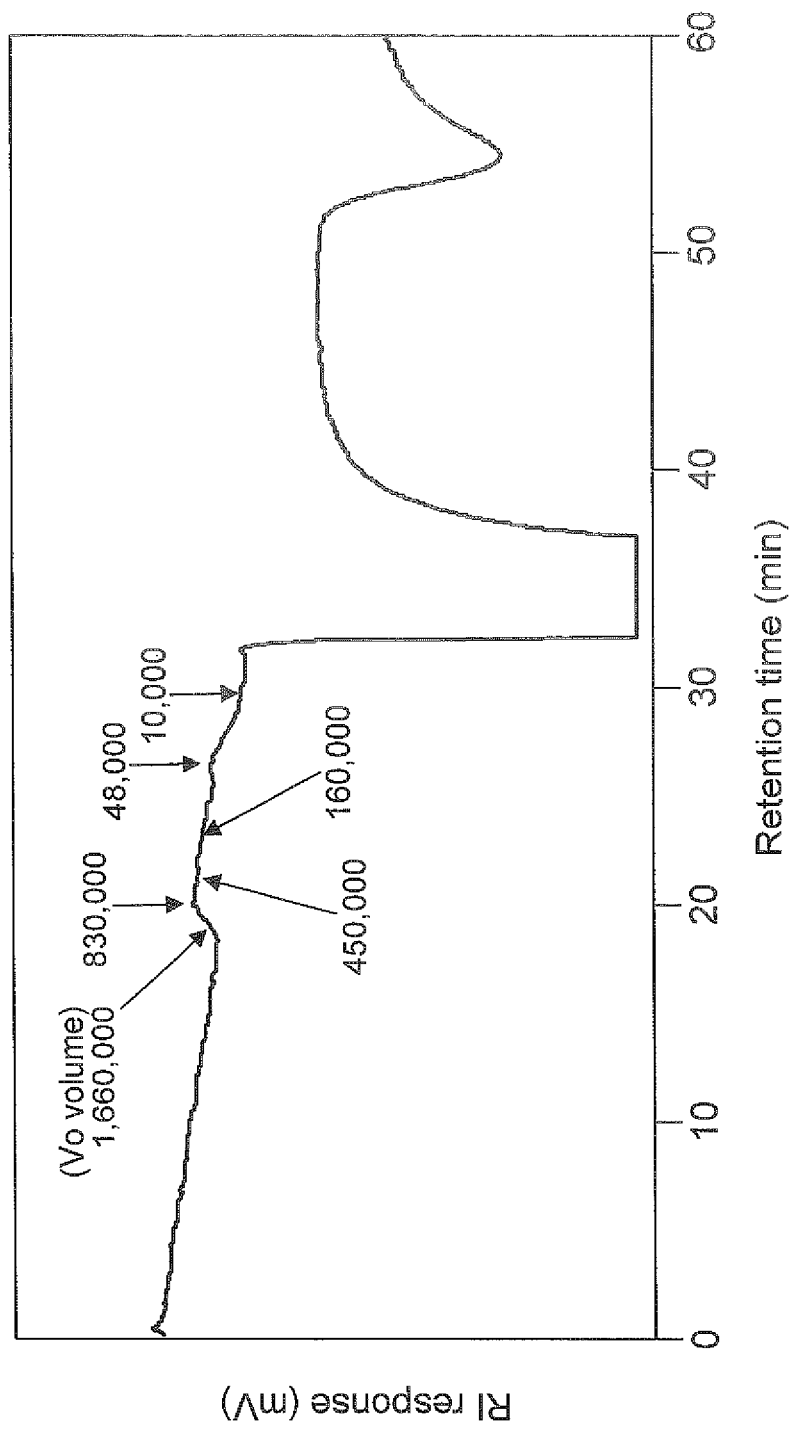
FIG. 8 is an HPSEC chart showing a molecular weight distribution of a heteroglycan fraction in Test Example 2.

Results of the analysis of the α-glucan fraction and the heteroglycan fraction are shown in Table 2 and Table 3. In addition, Results of the measurement of the molecular weight distribution of the α-glucan fraction and the heteroglycan fraction are shown in FIG. 7 and FIG. 8.

TABLE 2

| | Ethanol-precipitated fraction (SCE4) | α-Glucan fraction | Heteroglycan fraction |
|---|---|---|---|
| Peak molecular weight | Not determined | 900000 | 4800000 and 830000 |
| Carbohydrate (%) as Glc | 78.1 | 84.8 | 52.2 |
| Uronic acid (%) as GalA | 3.5 | 3.2 | 7.2 |
| Protein (%) as bovine gamma globulin | 35.2 | 5.0 | 5.9 |

TABLE 2-continued

| | Ethanol-precipitated fraction (SCE4) | α-Glucan fraction | Heteroglycan fraction |
|---|---|---|---|
| Component sugar proportion (mol. %) | | | |
| Ara | 20.8 | 2.2 | 24.7 |
| Rha | 1.8 | 1.4 | 3.3 |
| Fuc | 0.6 | 1.6 | 1.8 |
| Xyl | 10.0 | 1.5 | 9.9 |
| GlcA | 3.0 | 2.4 | 6.0 |
| GalA | 0.7 | — | 1.4 |
| Man | 4.0 | 3.4 | 11.3 |
| Gal | 14.1 | 3.6 | 9.5 |
| Glc | 45.0 | 83.9 | 32.1 |

TABLE 3

Sugar Linkage Pattern of α-Glucan Fraction and Heteroglycan Fraction

| | | Mol. % | |
|---|---|---|---|
| Sugar residue | Linkage pattern | α-Glucan fraction | Heteroglycan fraction |
| Arabinose | Nonreducing terminal (furanose) | — | 21.9 |
| | Nonreducing terminal (pyranose) | — | 7.2 |
| | 4- or 5-Linked | — | 7.5 |
| | 2-Linked (furanose) | — | 3.5 |
| Xylose | 4- or 5-Linked | — | 3.0 |
| | 3-Linked (pyranose) | — | 2.5 |
| Fucose | Nonreducing terminal | — | 3.1 |
| Mannose | Nonreducing terminal | 3.8 | 3.3 |
| | 2-Linked | 4.3 | — |
| | 3-Linked | 3.7 | 1.6 |
| | 4-Linked | — | 1.4 |
| | 4,6-Branched | — | 0.3 |
| Galactose | Nonreducing terminal | 5.3 | 7.3 |
| | 3-Linked | 3.4 | 3.4 |
| | 4-Linked | — | 0.9 |
| | 6-Linked | 3.2 | 4.8 |
| | 2,6-Branched | 2.1 | 1.3 |
| | 3,6-Branched | 3.0 | 9.3 |
| | 4,6-Branched | — | 0.6 |
| | 3,4,6-Branched | — | 1.9 |
| Glucose | Nonreducing terminal | 25.2 | 3.6 |
| | 3-Linked | 6.2 | 2.2 |
| | 4-Linked | 5.8 | 3.0 |
| | 6-Linked | 19.8 | 4.1 |
| | 2,6-Branched | 6.4 | 0.6 |
| | 4,6-Branched | 5.1 | 0.3 |
| | 3,4,6-Branched | 2.7 | — |
| Galacturonic acid | 2-Linked | — | 0.7 |
| Glucuronic acid | 4-Linked | — | 0.7 |

As shown in Table 2 and FIG. 7, the α-glucan fraction had a peak molecular weight of 900,000, and a molecular weight distributed within a range of 16,000 to a molecular weight corresponding to the Vo volume (about 1,660,000). In the α-glucan fraction, a proportion of glucose in the component sugars was about 84%. As shown in Table 2 and FIG. 8, the heteroglycan fraction had two peak molecular weights, 48,000 and 830,000. The molecular weight was distributed within a range of 10,000 to a molecular weight corresponding to the Vo volume (about 1,660,000). In the heteroglycan fraction, proportions of glucose and arabinose in the component sugars were about 32% and about 25%, respectively. The α-glucan fraction and the heteroglycan fraction were each a polysaccharide fraction containing sugar as a main component.

As shown in Table 3, the α-glucan fraction had characteristics of containing nonreducing terminal glucose and α-6-linked glucose (6-linked) in large amounts of about 25% and about 20%, respectively. The heteroglycan fraction had characteristics of containing nonreducing terminal arabinose in an amount of about 22%.

Example 1: Peyer's Patch Activating Effect Test

A Peyer's patch activating effect test was performed in the same manner as in Test Example 1 by using the α-glucan fraction (Fraction A1) and the heteroglycan fraction (Fraction X) prepared in Test Example 2 and the delignified SCE-4 and the ethanol-precipitated fraction (SCE-4) prepared in Test Example 1.

Figure 3:
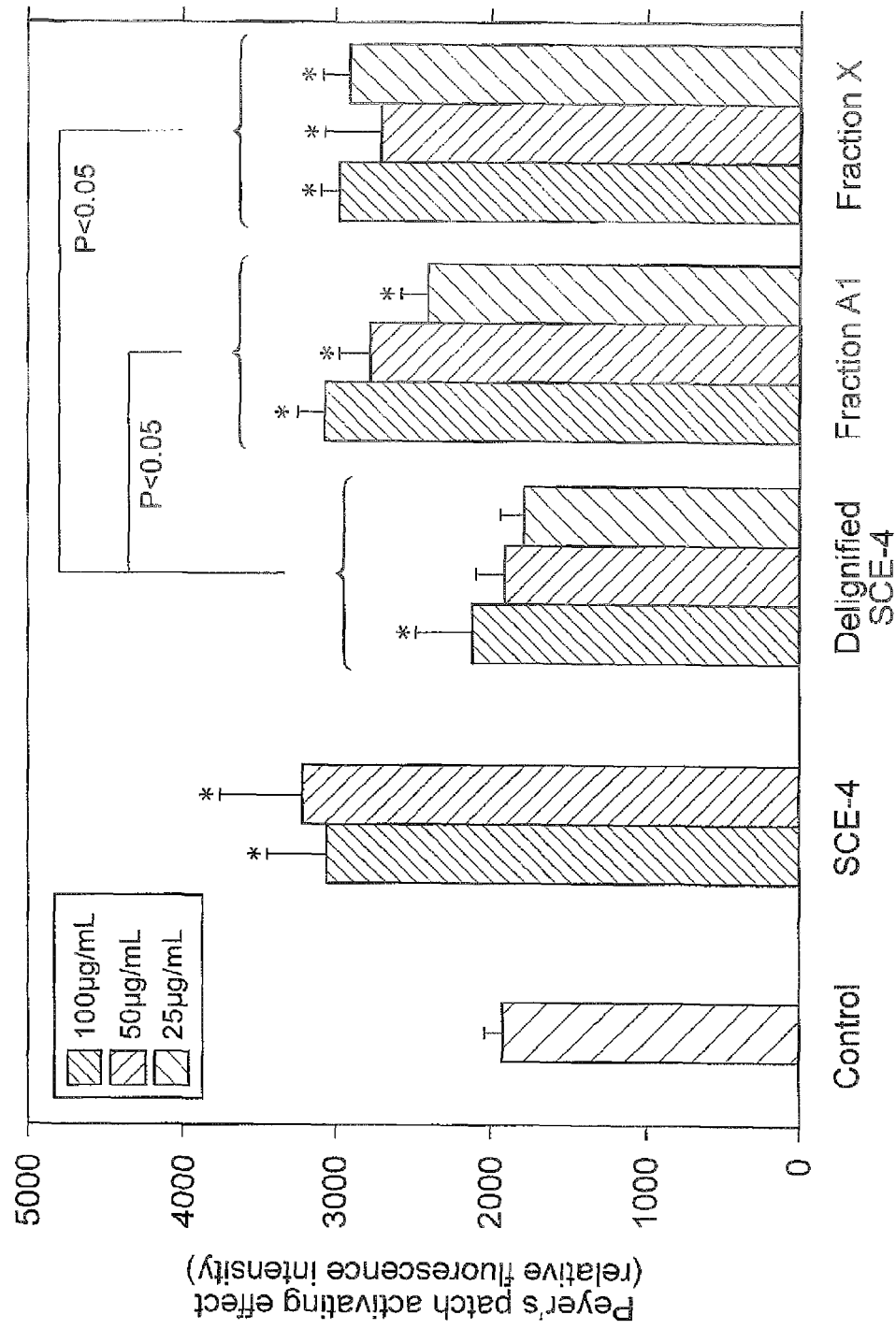
FIG. 3 is a graph showing results of a Peyer's patch activating effect test in Example 1.

FIG. 3 shows results of the Peyer's patch activating effect test. A bone marrow cell growth promoting factor amount is shown as the Peyer's patch activating effect. The α-glucan fraction (Fraction A1) and the heteroglycan fraction (Fraction X) at any loading (25 μg/mL, 50 μg/mL, 100 μg/mL) had a significantly higher Peyer's patch activating effect than the delignified SCE-4, and showed a Peyer's patch activation effect comparable to that of the ethanol-precipitated fraction (SCE-4).

The extract derived from sugar cane, which is a raw material, has a high salt content, and the yield of the ethanol-precipitated fraction (SCE-4) is about 5%. In addition, the ethanol-precipitated fraction (SCE-4) is a fraction having various polysaccharides mixed, and also contains a lignin component. Therefore, the ethanol-precipitated fraction is brownish red and difficult to form into a powder, and thus, has poor processing characteristics and astringency. Meanwhile, the α-glucan fraction and heteroglycan fraction obtained in the example are tasteless white powders, and thus easy to process.

Example 2: Participation of α-D-(1→6)-Glucan Structure in Peyer's Patch Activating Effect <Enzymatic Digestion of α-Glucan Fraction and Heteroglycan Fraction>

To a 25 mM acetate buffer (pH 4.5, 1 mg/mL) solution of the α-glucan fraction (1.5 mg) or the heteroglycan fraction (1.5 mg) were added exo-α-L-arabinofuranosidase (20 μL), exo-β-D-(1→3)-galactanase (20 μL), and endo-β-D-(1→4)-galactanase (5 μL), followed by enzyme reaction under conditions of 37° C. for 2 days. The obtained digest was heat-treated for 30 seconds in a boiling water bath to deactivate the enzyme. To a half of this enzyme reaction liquid (shown as "1,3/1,4-galactanase" in FIG. 4) was further added dextranase (0.25 units), followed by incubation for 2 days at 37° C., and subsequently, the enzyme was deactivated under the same conditions as the above to obtain an enzyme reaction liquid (shown as "dextranase" in FIG. 4). These reaction liquids were preserved at −20° C. until use.

<Measurement of Amount of IL-6 Production>

Preparation and culture of mouse Peyer's patch cells were performed in the same manner as in Test Example 1.

(Enzyme Immunoassay (ELISA))

An anti-mouse IL-6 primary antibody diluted to 1 μg/mL with a 50 mM carbonate-bicarbonate buffer (pH 9.6) (100 μL/well) was dispensed into an ELISA plate (Immuno-Maxisorp, Nunc) and incubated at 4° C. overnight. The plate was washed three times with a phosphate-buffered physiological saline (PBST) containing 0.05% Tween 20 (300 μL/well) and subsequently incubated at 37° C. for 1 hour using PBST containing 1% skim milk (SM) (SM-PBST) (100 μL/well). The plate was washed four times with PBST (300 μL/well), followed by addition of 1% SM-PBST was added (50 μL/well) and preincubation for 10 minutes at room temperature, and then, the Peyer's patch culture supernatant was added (50 μL/well), followed by incubation at 4° C. overnight. The plate was washed three times with PBST (300 μL/well) and preincubated for 10 minutes at room temperature using 1% SM-PBST (100 μL/well). Further, a biotin-labelled anti-IL-6 secondary antibody diluted with 1% SM-PBST (1:1000, 50 μL/well) was added to the plate, and after incubation at 37° C. for 1 hour, the plate was washed three times with PBST (300 μL/well). The plate was preincubated for 10 minutes at room temperature using 1% SM-PBST (100 μL/well), and subsequently, alkaline-phosphatase-labelled streptavidin diluted with 1% SM-PBST (1:1000, 100 μL/well) was added, followed by incubation at 37° C. for 1 hour. The plate was washed five times with PBST (300 μL/well), and subsequently a substrate solution [a 10% diethanolamine buffer (pH 9.8) solution of disodium p-nitrophenyl phosphate](1 mg/mL, 150 μL/well) was added, followed by incubation at room temperature. The developed yellow color was measured using a microplate reader (Multiskan JX, Thermo Electron Corp.) (measurement wavelength; 405 nm, blank wavelength; 492 nm).

<Results>

Figure 4:
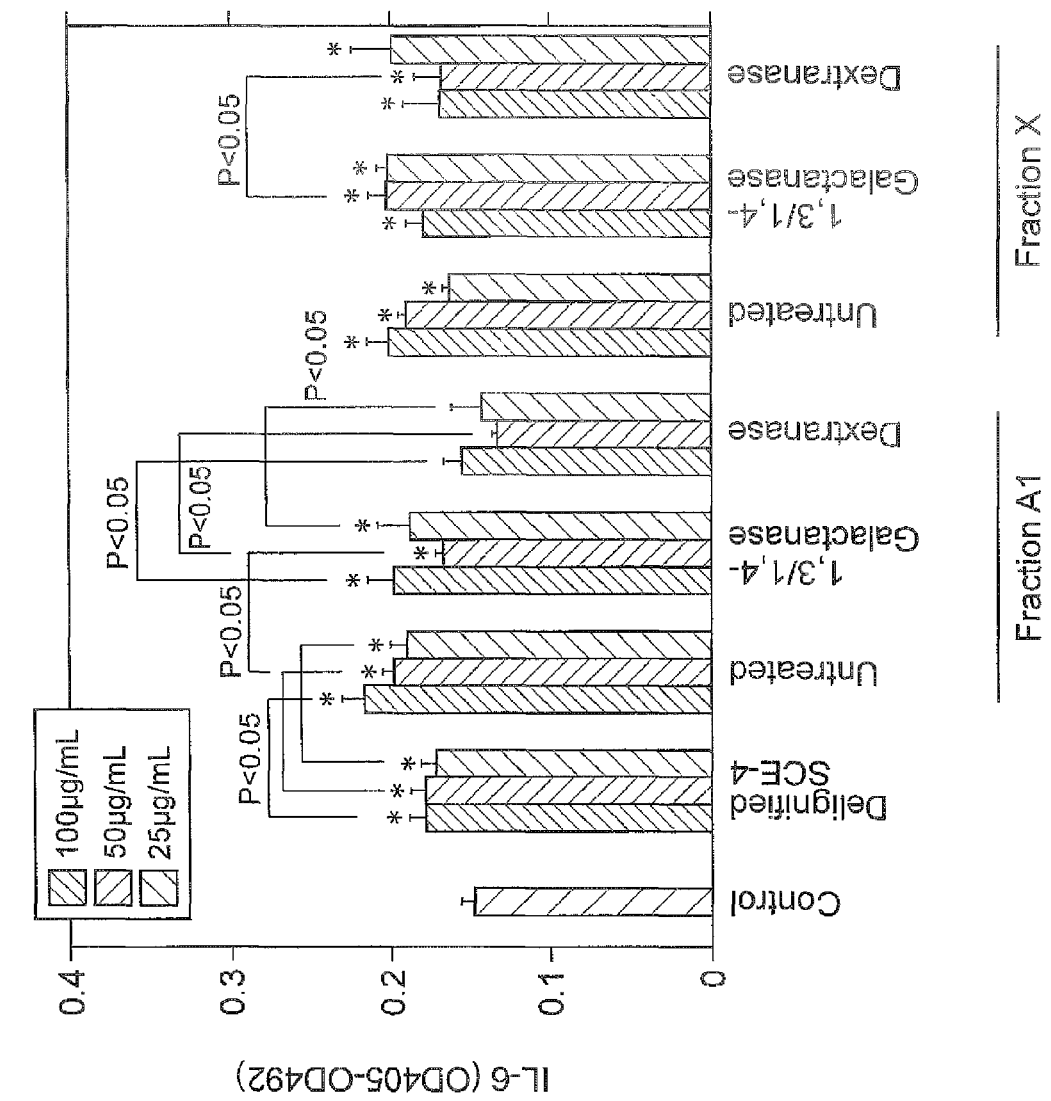
FIG. 4 is a graph showing results of an IL-6 production induction test in Example 2.

It has been revealed that IL-6 is relevant to a Peyer's patch activating effect as one of bone marrow cell growth promoting factors. FIG. 4 shows results of the IL-6 production induction test. In the case of the delignified SCE-4, the amount of IL-6 production significantly increased as compared with the control ("delignified SCE-4" in FIG. 4). The IL-6 production enhancing ability was also observed in the α-glucan fraction (Fraction A1 in FIG. 4) and the heteroglycan fraction (Fraction X in FIG. 4) (in FIG. 4, "Untreated" of the α-glucan fraction and the heteroglycan fraction). In addition, the IL-6 production enhancing activity of the α-glucan fraction and the heteroglycan fraction was not decreased even by the 1,3/1,4-galactanase treatment. This shows that these galactans are not a structure necessary for the expression of activity. Meanwhile, when a dextranase treatment was performed after the galactanase treatment, the activity of the α-glucan fraction decreased to the same extent as that of the control. In addition, the activity of the heteroglycan fraction also decreased at a concentration of 50 μg/ml. Dextranase has activity of recognizing and cleaving a glucan structure of an α-1,6-linked tri- or higher saccharide. Therefore, it was suggested that a polysaccharide having such a saccharide chain structure is contained in the α-glucan fraction and the heteroglycan fraction, and contributes to the IL-6 production enhancing activity. Incidentally, in the case where dextran was added alone and the test was performed, no change in the amount of IL-6 production was observed (data not shown).

Example 3: Oral Administration Test of Polysaccharide Fraction in Rodent Malaria Parasite (Chloroquine-Sensitive Strain) Infection Model Using the α-glucan fraction, the heteroglycan fraction, and the ethanol-precipitated fraction (SCE-4) prepared in Production Example 1 as polysaccharide fractions, an oral administration test of the polysaccharide fractions in a rodent malaria parasite infection model was performed.

<*Plasmodium berghei* N (Chloroquine-Sensitive Strain) Infection Model>

A rodent malaria parasite infection experiment was performed in Kitasato University, Kitasato Institute for Life Sciences, Research Center for Tropical Disease. An animal experiment was performed according to the Safety and Health Manager Regulations for Handing Experimental Animals of Kitasato Institute (legally incorporated educational institution) specified in accordance with the relevant laws and notifications from the relevant ministries, etc.

ICR mice (low 20 grams) purchased from Charles River Japan, Inc. were preliminarily kept for one week under fixed conditions of a room temperature of 23±2° C. and a humidity of 55±10% with a lighting time of 9 hours/day, and subsequently subjected to the experiment.

A rodent malaria parasite was maintained as follows: a frozen rodent malaria parasite *Plasmodium berghei* N (chloroquine-sensitive strain) was thawed and intraperitoneally administered to the ICR mice (200 μL/mouse) to cause infection, and in a few days after the infection, blood was collected from the heart and administered to the tail veins of other mice (four to five) (200 μL/mouse) to repeatedly cause infection.

Parasite-infected erythrocytes were prepared as follows. That is, a mouse with high efficiency of infection was selected, and blood was collected from the heart under Nembutal anesthesia to make a blood smear. The smear was stained by the simple Giemsa staining method using a QuickIII staining kit (astradiagnosics) or Hemacolor (Merck), and an infection rate (Parasitemia %) was calculated. The collected blood was diluted with physiological saline for injection, and the number of erythrocytes was counted by an hemocytometer and multiplied by the infection rate to calculate the number of infected erythrocytes. The blood was diluted with physiological saline to give an infected erythrocyte suspension having $1\times10^5$ or $1\times10^7$ cells/mL, and subsequently administered to the tail vein in an amount of 200 μL/mouse.

The rodent malaria parasite infection experiment on mice was performed by intravenously injection with the $2\times10^4$ cells of *P. berghei* N-infected erythrocytes into the tail veins of male ICR mice (0.2 ml/mouse).

<Oral Administration of Polysaccharide to Infection Model Mouse>

Figure 5:
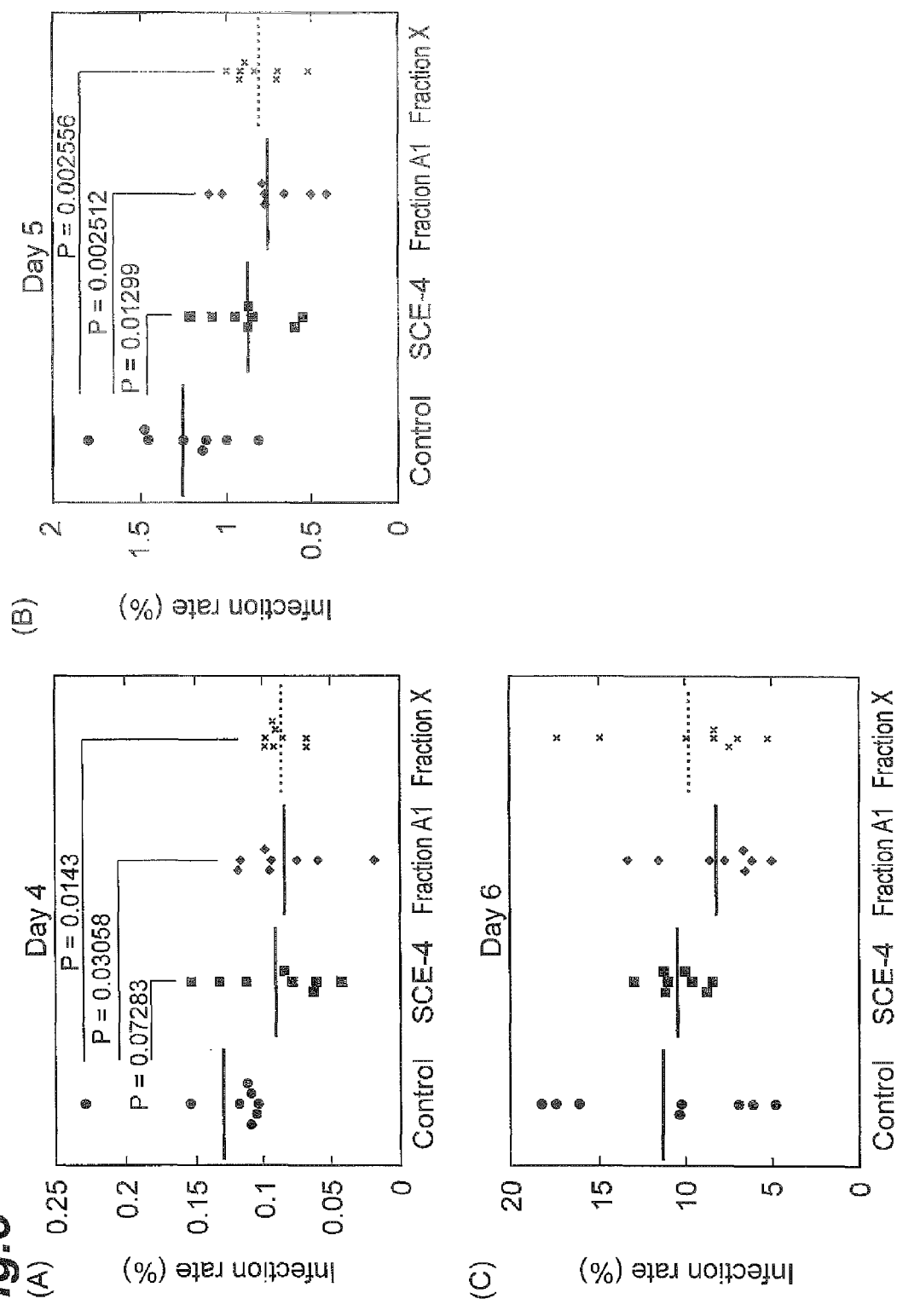
FIGS. 5(A) to 5(C) are graphs showing results of an oral administration test of polysaccharide fractions in a rodent malaria parasite (chloroquine-sensitive strain) infection model in Example 3.

The α-glucan fraction (Fraction A1 in FIGS. 5(A) to 5(C)), the heteroglycan fraction (Fraction X in FIGS. 5(A) to 5(C)), and SCE-4 were orally administered to the ICR mice each day in a dose of 500 μL/mouse using a feeding needle. A dosage of the ethanol-precipitated fraction (SCE-4) was set at 600 mg/kg/day, and dosages of the α-glucan fraction and the heteroglycan fraction were set at 28 mg/kg/day and 22 mg/kg/day, respectively. The dosages of the α-glucan fraction and the heteroglycan fraction are each an amount corresponding to 600 mg/kg/day of SCE-4 calculated from the yield. As a control, water was orally administered alone. Administration was started 7 days before parasite infection and continued even after the *plasmodium* infection.

<Calculation of Rodent Malaria Parasite Infection Rate>

Three days after infection, blood was collected from the tail of a mouse to make a blood smear. The smear was stained by the simple Giemsa staining method using a QuickIII staining kit (astradiagnosics) or Hemacolor (Merck). Immersion oil was dropped on the smear, and the smear was observed under a microscope (ORIMPUS BX40) according to criteria shown in Table 4.

TABLE 4

| Infection rate | The number of fields enumerated |
| --- | --- |
| More than 20% | Three fields |
| More than 10% and 20% or less | Five fields |
| More than 2% and 10% or less | Ten fields |

TABLE 4-continued

| Infection rate | The number of fields enumerated |
| --- | --- |
| More than 0.05% and 2% or less | Twenty fields |
| 0.05% or less | Fifty fields |

In addition, the infection rate of erythrocytes (Parasitemia) was calculated by applying the following equation.

$$\frac{\text{Number of infected erythrocytes}}{\text{Total number of erythrocytes}} \times 100 = \quad \text{[Equation 1]}$$

Infection rate(Parasitemia)

<Results>

FIGS. 5(A) to 5(C) show results of the oral administration test of the polysaccharide fractions in the rodent malaria parasite infection model. In the mice to which the ethanol-precipitated fraction (SCE-4) was administered, the infection rate significantly decreased on Day 4 and Day 5 as compared with the control. In addition, in the mice to which the α-glucan fraction (Fraction A1 in FIGS. 5(A) to 5(C)) was administered and the mice to which the heteroglycan fraction (Fraction X in FIGS. 5(A) to 5(C)) was administered, although the dosages of the α-glucan fraction and the heteroglycan fraction were obviously smaller than that of SCE-4 (about ¹/₂₀), the infection rate significantly decreased on Day 4 and Day 5 as compared with the control (FIGS. 5(A) to 5(C), p values in Fisher's LSD test). Further, in the five mice out of the eight mice to which the α-glucan was administered, the effect lasted even on Day 6. From the above, it was confirmed that the protective effect against malaria infection shown by the ethanol-precipitated fraction (SCE-4) is expressed by the α-glucan and heteroglycan contained. In addition, the results of the example show that although the dosages of the α-glucan fraction and the heteroglycan fraction are smaller than that of SCE-4 (about ¹/₂₀), the α-glucan fraction and the heteroglycan fraction each have a protective effect against malaria infection nearly equal to or slightly higher than SCE-4. Therefore, a protective effect against malaria infection remarkably higher than that of SCE-4 can be expressed by increasing the dosages of the α-glucan fraction and the heteroglycan fraction.

Example 4: Oral Administration Test 2 of Polysaccharide Fraction in Rodent Malaria Parasite (Chloroquine-Resistant Strain) Infection Model Using the ethanol-precipitated fraction (SCE-4) prepared in Production Example 1 as a polysaccharide fraction, an oral administration test of the polysaccharide fraction in a rodent malaria parasite infection model was performed.

<*Plasmodium yoelii* NS Infection Model>

Using a rodent malaria parasite *Plasmodium yoelii* NS (chloroquine-resistant strain), parasite infection was caused by tail vein administration, immediately followed by subcutaneous administration of chloroquine (an aqueous solution of Chloroquine diphosphate salt) to mice in a dose of 60 mg/kg/mouse to maintain a resistant parasite. The number of infected erythrocytes intravenously injected to the tail vein was set at $2\times10^6$ cells. Other procedures were performed in the same manner as in <*Plasmodium berghei* N Infection Model> of Example 3.

<Oral Administration of Polysaccharide to Infection Model Mouse>

SCE-4 was orally administered to ICR mice each day in a dose of 500 μL/mouse using a feeding needle. A dosage of SCE-4 was set at 600 mg/kg/day. As a control, water was orally administered alone. Administration was started 7 days before parasite infection and continued even after the *plasmodium* infection.

<Calculation of Rodent Malaria Parasite Infection Rate>

Calculation was performed in the same manner as in Example 3.

<Results>

Figure 9:
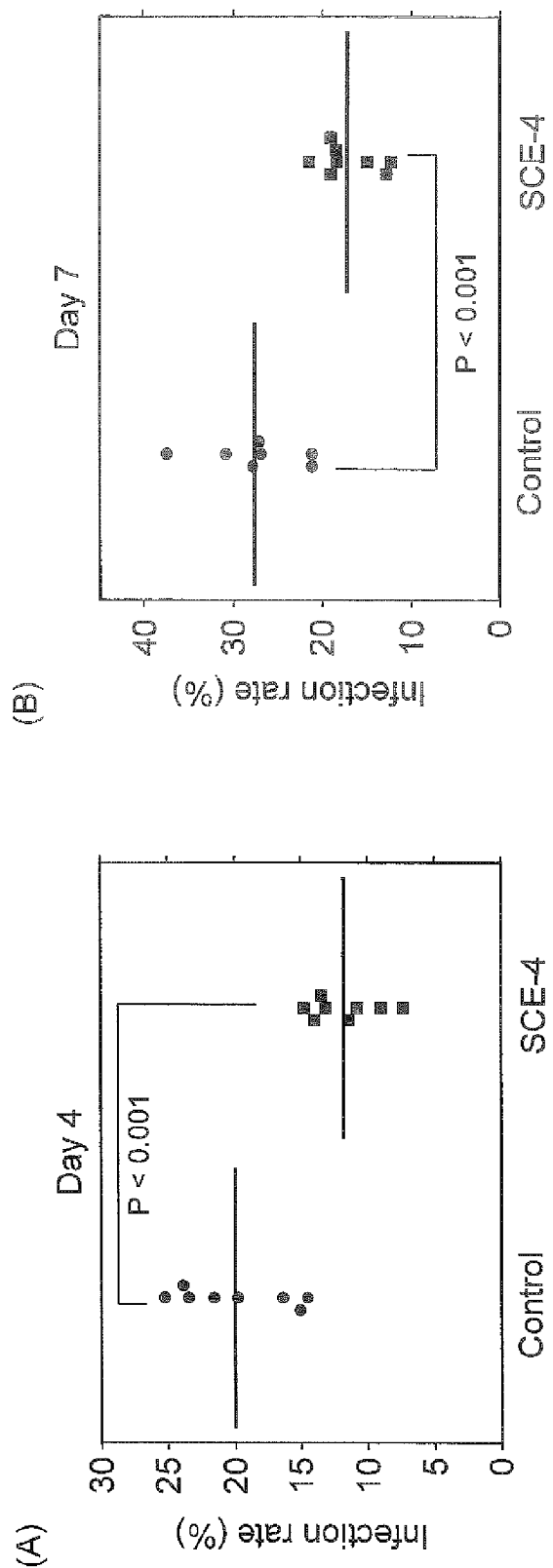
FIGS. 9(A) and 9(B) are graphs showing results of an oral administration test of a polysaccharide fraction in a rodent malaria parasite (chloroquine-resistant strain) infection model in Example 4.

Results of the oral administration test are shown in FIGS. 9(A) and 9(B). In the mice to which the ethanol-precipitated fraction (SCE-4) was administered, the infection rate significantly decreased on Day 4 and Day 7 as compared with the control (p values in Fisher's LSD test were all p<0.001).

Example 5: Oral Administration Test of Polysaccharide Fraction in Combination with Antimalarial Agent in Rodent Malaria Parasite (Chloroquine-Resistant Strain) Infection Model Using the ethanol-precipitated fraction (SCE-4) prepared in Production Example 1 as a polysaccharide fraction, the combined effect with an antimalarial agent artesunate (Artesnate, abbreviated to AN) was tested by an oral administration test in a rodent malaria parasite infection model.

<*Plasmodium yoelii* NS Infection Model>

A procedure was performed in the same manner as in Example 4, except that the number of *P. yoelii* NS-infected erythrocytes intravenously injected to the tail vein was changed from $2 \times 10^6$ cells to $2 \times 10^4$ cells.

<Oral Administration of Polysaccharide and AN to Infection Model Mouse>

SCE-4 and AN were orally administered to ICR mice each day in a dose of 500 μL/mouse using a feeding needle. A dosage of SCE-4 was 600 mg/kg/day, and AN was dissolved in a 10% dimethylsulfoxide (DMSO) aqueous solution containing 0.5% Tween 80 and administered in a dosage of 3 mg/kg/day. The administration of SCE-4 was started 7 days before parasite infection and continued even after the *plasmodium* infection. The administration of AN was started 2 hours after the parasite infection and continued until Day 3 after the *plasmodium* infection (four times in total). In addition, SCE-4 was administered 3 hours or more after the administration of AN.

To a control group, water and a 10% DMSO aqueous solution containing 0.5% Tween 80 were orally administered, and to AN3 groups, water and a 10% DMSO aqueous solution of AN containing 0.5% Tween 80 were orally administered, and to SCE-4+AN3 groups, an SCE-4 aqueous solution and a 10% DMSO aqueous solution of AN containing 0.5% Tween 80 were orally administered.

<Calculation of Rodent Malaria Parasite Infection Rate>

Calculation was performed in the same manner as in Example 3.

<Results>

Results of the oral administration test are shown in FIGS. 10(A) to 10(C). In the AN3 group to which AN was administered, the infection rate significantly decreased on Day 4 and Day 5 as compared with the control group (p values in Dunnett's test were p<0.001 and p=0.0024, respectively). In the SCE-4+AN3 group using SCE-4 in combination with AN, the infection rate significantly decreased on Day 4 and Day 5 as compared with the control group (p values in Dunnett's test were p<0.001 and p=0.0002, respectively), and also the effect still lasted on Day 6 (p value in Dunnett's test was p=0.0047). As is clear from these results, the protective effect against malaria infection was increased by using SCE-4 in combination with AN. This shows that the effect of SCE-4 does not compete with the effect of the existing antimalarial agent (AN). Therefore, SCE-4 can be used as an alternative drug for an existing antimalarial agent suffering from the appearance of a resistant strain, or can be used in combination with an existing antimalarial agent.

The invention claimed is:

1. A Peyer's patch activator, comprising a polysaccharide fraction obtained from sugar cane as an active ingredient,
   wherein the polysaccharide fraction comprises α-glucan or heteroglycan as a main component, and
   the polysaccharide fraction is obtained by ethanol-precipitating a raw material selected from a sugar cane extract and a molasses derived from sugar cane, and removing low-molecular-weight substances from the obtained precipitate by dialysis or a membrane process.

2. The Peyer's patch activator according to claim 1, wherein the raw material is the sugar cane extract.

3. The Peyer's patch activator according to claim 1, wherein
   the polysaccharide fraction comprising the heteroglycan as the main component,
   the polysaccharide fraction has peak molecular weights within a range of 38,400 to 57,600 and within a range of 664,000 to 996,000,
   a proportion of glucose in all component sugars in the polysaccharide fraction is 30 to 50%,
   a proportion of arabinose in all component sugars in the polysaccharide fraction is 20 to 30%, and
   a proportion of nonreducing terminal arabinose is 20 to 30%.

4. The Peyer's patch activator according to claim 3,
   wherein the raw material is an extract derived from sugar cane, and
   the extract is a fraction which absorbs light at a wavelength of 420 nm and from which sucrose, glucose, and fructose are excluded, among a large number of fractions obtained by passing a sugar cane extract or a molasses derived from sugar cane through a column filled with a cation exchange resin as a carrier and performing fractionation by a difference in affinity between the cation exchange resin and each component using water as an eluent.

5. The Peyer's patch activator according to claim 3,
   wherein the polysaccharide fraction is a fraction obtained by passing the ethanol-precipitated fraction through a column filled with an anion exchange resin as a carrier, and eluting components adsorbed on the anion exchange resin with an elution solvent having a high ionic strength.

6. The Peyer's patch activator according to claim 3, wherein the polysaccharide fraction consists of:
   a fraction other than a fraction in an amount corresponding to void volume of first outflow resulting from passing the ethanol-precipitated fraction through a column filled with an anion exchange resin equilibrated with water as a carrier, eluting components adsorbed on the anion exchange resin with 100 mM $NH_4HCO_3$ and subsequently with 300 mM $NH_4HCO_3$ to obtain eluted fractions, and further passing the obtained eluted fractions through a gel filtration column having a molecular cutoff of $1 \times 10^4$ to $1 \times 10^6$ Da; and
   a fraction in an amount corresponding to void volume of first outflow resulting from passing the ethanol-precipitated fraction through a column filled with an anion exchange resin equilibrated with water as a carrier, eluting components adsorbed on the anion exchange resin with 300 mM NH$_4$HCO$_3$ and subsequently with 1.8 M NH$_4$HCO$_3$ to obtain eluted fractions, and further passing the obtained eluted fractions through a gel filtration column having a molecular cutoff of 2×10$^3$ to 4×10$^5$ Da.

7. A Peyer's patch activator, comprising a polysaccharide fraction obtained from sugar cane as an active ingredient,
wherein the polysaccharide fraction comprises α-glucan as a main component,
the polysaccharide fraction has a peak molecular weight within a range of 720,000 to 1,080,000,
a proportion of glucose in all component sugars in the polysaccharide fraction is 80% or more,
a proportion of nonreducing terminal glucose in the polysaccharide fraction is 20 to 30%,
a proportion of α-1,6-linked glucose in the polysaccharide fraction is 15 to 25%, and
the polysaccharide fraction is obtained from an ethanol-precipitated fraction obtained by
(i) ethanol-precipitating at least one raw material selected from a sugar cane extract and a molasses derived from sugar cane, and
(ii) removing low-molecular-weight substances from the obtained precipitate by dialysis or a membrane process.

8. The Peyer's patch activator according to claim 7,
wherein the raw material is an extract derived from sugar cane, and
the extract is a fraction which absorbs light at a wavelength of 420 nm and from which sucrose, glucose, and fructose are excluded, among a large number of fractions obtained by passing a sugar cane extract or a molasses derived from sugar cane through a column filled with a cation exchange resin as a carrier and performing fractionation by a difference in affinity between the cation exchange resin and each component using water as an eluent.

9. The Peyer's patch activator according to claim 7,
wherein the polysaccharide fraction is a fraction obtained by passing the ethanol-precipitated fraction through a column filled with an anion exchange resin as a carrier, eluting components adsorbed on the anion exchange resin with an elution solvent having a low ionic strength to obtain eluted fractions, and further gel-filtering the obtained eluted fractions.

10. The Peyer's patch activator according to claim 7,
wherein the polysaccharide fraction is a fraction in an amount corresponding to void volume of first outflow resulting from passing the ethanol-precipitated fraction through a column filled with an anion exchange resin equilibrated with water as a carrier, eluting components adsorbed on the anion exchange resin with 100 mM NH$_4$HCO$_3$ to obtain eluted fractions, and further passing the obtained eluted fractions through a gel filtration column having a molecular cutoff of 2×10$^3$ to 4×10$^5$ Da.

11. The Peyer's patch activator according to claim 7,
wherein the activator is an intestinal immune enhancer.

12. The Peyer's patch activator according to claim 7,
wherein the activator is a preventive/therapeutic agent for *plasmodium* infection.

13. A food product comprising the Peyer's patch activator according to claim 7.

14. An animal food product comprising the Peyer's patch activator according to claim 7.

15. A medicinal composition comprising the Peyer's patch activator according to claim 7 present in an amount effective to treat a *plasmodium* infection in a human subject, or in an amount effective to ameliorate or reduce a rate of infection of a *plasmodium* infection in a human subject.

16. The medicinal composition according to claim 15,
wherein the medicinal composition further comprises at least one antimalarial agent selected from the group consisting of quinine, mefloquine, sulfadoxine, pyrimethamine, chloroquine, primaquine, artesunate, artemether, and lumefantrine.

17. The medicinal composition according to claim 16,
wherein the antimalarial agent is artesunate.

18. A method of treating *plasmodium* infection in a subject, comprising administering to the subject the medicinal composition according to claim 15.

* * * * *